United States Patent
Bindra et al.

(10) Patent No.: US 8,716,251 B2
(45) Date of Patent: *May 6, 2014

(54) PHARMACEUTICAL FORMULATIONS CONTAINING AN SGLT2 INHIBITOR

(71) Applicant: Bristol-Myers Squibb Company, Princeton, NJ (US)

(72) Inventors: Dilbir S. Bindra, New Brunswick, NJ (US); Mandar V. Dali, Bridgewater, NJ (US); Prakash V. Parab, New Brunswick, NJ (US); Jatin M. Patel, New Brunswick, NJ (US); Li Tao, New Brunswick, NJ (US); Ravindra W. Tejwani, New Brunswick, NJ (US); Nipa Vatsaraj, New Brunswick, NJ (US); Yongmei Wu, New Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/734,655

(22) Filed: Jan. 4, 2013

(65) Prior Publication Data

US 2013/0129819 A1    May 23, 2013

Related U.S. Application Data

(60) Continuation of application No. 13/529,463, filed on Jun. 21, 2012, now Pat. No. 8,361,972, which is a division of application No. 12/949,473, filed on Nov. 18, 2010, now Pat. No. 8,221,786, which is a division of application No. 12/053,442, filed on Mar. 21, 2008, now Pat. No. 7,851,502.

(60) Provisional application No. 60/896,286, filed on Mar. 22, 2007.

(51) Int. Cl.
*A61K 9/48* (2006.01)
*A61K 31/70* (2006.01)
*A61K 9/30* (2006.01)
*A61P 3/00* (2006.01)
*A61P 9/00* (2006.01)

(52) U.S. Cl.
USPC ............. 514/23; 424/452; 424/465; 424/451; 514/460

(58) Field of Classification Search
None
See application file for complete search history.

(56) References Cited

U.S. PATENT DOCUMENTS

| | | | |
|---|---|---|---|
| 6,342,249 B1 * | 1/2002 | Wong et al. | .................. 424/473 |
| 6,414,126 B1 | 7/2002 | Ellsworth et al. | |
| 6,515,117 B2 | 2/2003 | Ellsworth et al. | |
| 6,774,112 B2 | 8/2004 | Gougoutas | |
| 7,030,162 B2 | 4/2006 | Plachetka et al. | |
| 7,164,015 B2 | 1/2007 | Shen et al. | |
| 7,375,213 B2 | 5/2008 | Deshpande et al. | |
| 7,919,598 B2 | 4/2011 | Gougoutas et al. | |
| 2001/0033864 A1 * | 10/2001 | Colonno et al. | ............. 424/451 |
| 2007/0015841 A1 | 1/2007 | Tawa et al. | |
| 2008/0004336 A1 | 1/2008 | Gougoutas et al. | |

FOREIGN PATENT DOCUMENTS

| | | |
|---|---|---|
| WO | WO 03/099836 | 12/2003 |
| WO | WO 2008/002824 | 1/2008 |

OTHER PUBLICATIONS

Meng Wei et al., "Discovery of Dapagliflozin: A potent selective renal sodium-dependent glucose contransporter 2 (SGLT2) inhibitor for the treatment of type 2 diabetes," Journal of Medicinal Chemistry, vol. 51, No. 5, Mar. 2008, pp. 1145-1149.

* cited by examiner

*Primary Examiner* — Scott Long
*Assistant Examiner* — Sarah Alawadi
(74) *Attorney, Agent, or Firm* — McDonnell Boehnen Hulbert & Berghoff LLP

(57) ABSTRACT

Pharmaceutical formulations are provided which are in the form of capsules or tablets for oral use and which include a medicament dapagliflozin or its propylene glycol hydrate

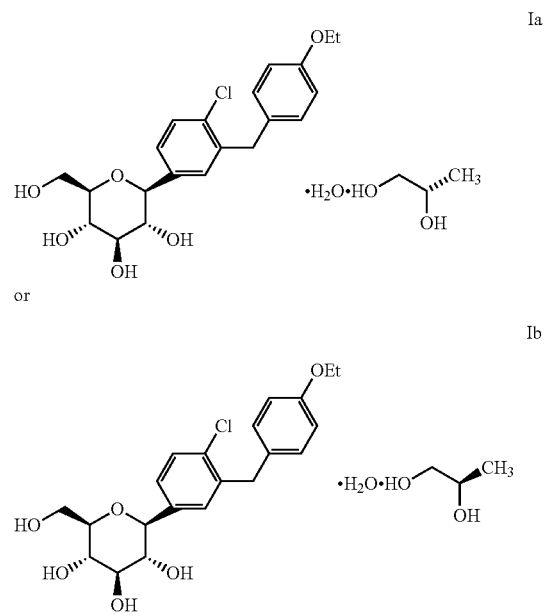

and a pharmaceutical acceptable carrier therefor, which formulation is designed for immediate release.

38 Claims, No Drawings

PHARMACEUTICAL FORMULATIONS CONTAINING AN SGLT2 INHIBITOR

This application is a continuation of U.S. patent application Ser. No. 13/529,463, which is a divisional of U.S. patent application Ser. No. 12/949,473, which is a divisional of U.S. patent application Ser. No. 12/053,442, each of which is hereby incorporated herein by reference in its entirety, and the priority of each of which under 35 U.S.C. §120 is hereby claimed. U.S. patent application Ser. No. 12/053,442 claims priority to U.S. Provisional Patent Application Ser. No. 60/896,286, filed on Mar. 22, 2007, which is hereby incorporated herein by reference in its entirety, and the priority of which under 35 U.S.C. §119 is hereby claimed.

FIELD OF THE INVENTION

The present invention provides an immediate release pharmaceutical formulation which includes a tablet or capsule formulation containing the sodium dependent glucose transporter (SGLT2) inhibitor dapagliflozin or its propylene glycol hydrate.

BACKGROUND OF THE INVENTION

At least 171 million people worldwide suffer from type II diabetes (NIDDM), which is characterized by hyperglycemia due to excessive hepatic glucose production and peripheral insulin resistance. Hyperglycemia is considered to be the major risk factor for the development of diabetic complications, and is likely to contribute directly to the impairment of insulin secretion seen in advanced NIDDM. Thus, consistent control of plasma glucose levels in NIDDM patients can offset the development of diabetic complications and beta cell failure seen in advanced disease. Plasma glucose is normally filtered in the kidney in the glomerulus and actively reabsorbed in the proximal tubule. SGLT2 appears to be the major transporter responsible for the reuptake of glucose at this site. A selective inhibitor of the sodium-dependent glucose transporter SGLT2 in the kidney is expected to normalize plasma glucose levels by enhancing the excretion of glucose in the urine, thereby improving insulin sensitivity, and delaying the development of diabetic complications.

The compound of the structure (I)

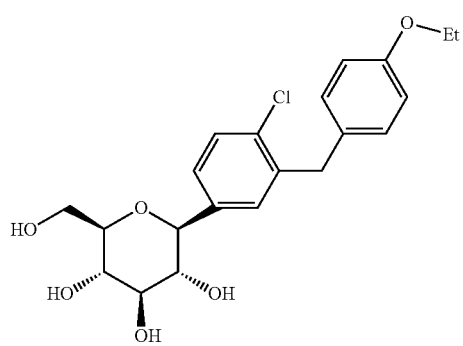

or pharmaceutically acceptable salts or solvates thereof (hereinafter dapagliflozin), an orally active SGLT2 inhibitor is disclosed in U.S. Pat. No. 6,515,117 (the disclosure of which is incorporated herein by reference in its entirety).

U.S. application Ser. No. 11/765,481 filed Jun. 28, 2007, published as US 2008-0004336 A1 discloses dapagliflozin in the form of its (S)-propylene glycol ((S)-PG) hydrate and its (R)-propylene glycol ((R)-PG) hydrate. The (S)-propylene glycol hydrate is referred to as form SC-3 and has the structure shown as (Ia).

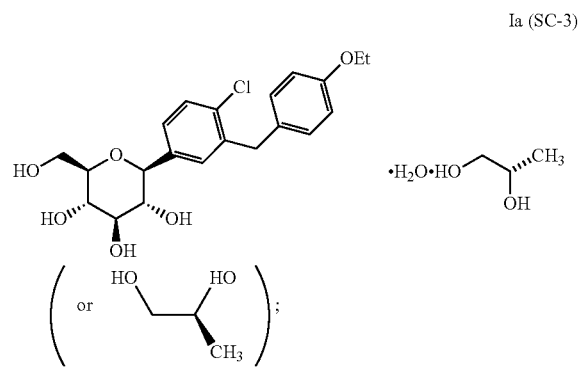

The (R)-propylene glycol hydrate is referred to as form SD-3 and has the structure shown as (Ib).

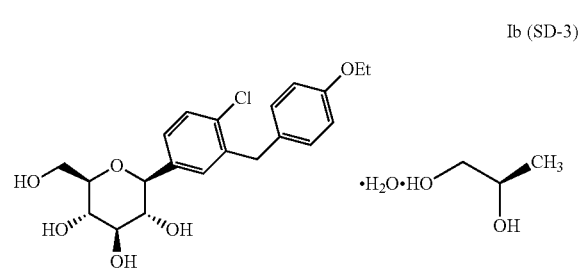

Methods for preparing the (S)-PG hydrate and the (R)-PG hydrate of dapagliflozin are provided in U.S. application Ser. No. 11/765,481 filed Jun. 28, 2007, published as US 2008-0004336 A1 (the disclosure of which is incorporated herein by reference in its entirety).

BRIEF DESCRIPTION OF THE INVENTION

In accordance with the present invention, pharmaceutical formulations are provided which can be in the form of a capsule formulation or a tablet formulation, for oral use, designed for immediate release, and include as the medicament dapagliflozin which has the structure (I)

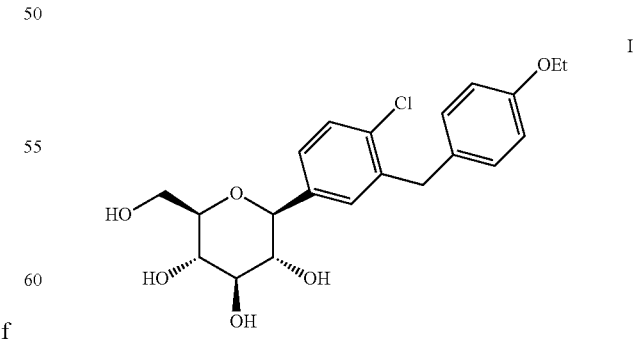

or a pharmaceutically acceptable salt, solvate, mixed solvate, or complex thereof (which is disclosed in U.S. Pat. No. 6,515,117 herein incorporated by reference in its entirety) and a pharmaceutically acceptable carrier thereof.

In one embodiment, the dapagliflozin is in the form of its (S)-propylene glycol ((S)-PG) hydrate (SC-3) which is shown as Compound (Ia)

Compound Ia

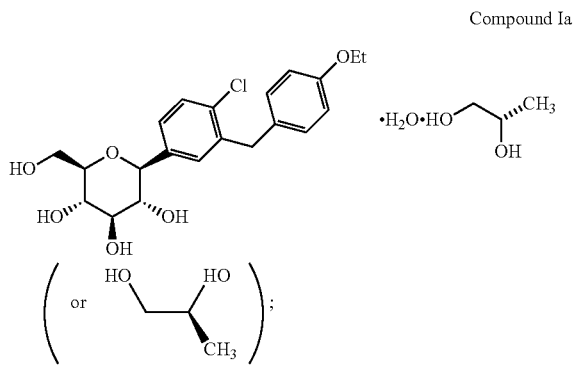

the preparation for which is disclosed in U.S. application Ser. No. 11/765,481, filed Jun. 28, 2007, U.S. Publication No. 2008-0004336 A1, and Provisional Application No. 60/817,118, filed Jun. 28, 2006, the disclosures of both of which are incorporated herein by reference in their entireties.

In another embodiment, the dapagliflozin is in the form of its (R)-propylene glycol ((R)-PG) hydrate (SD-3), which is shown as Compound (Ib)

Compound Ib

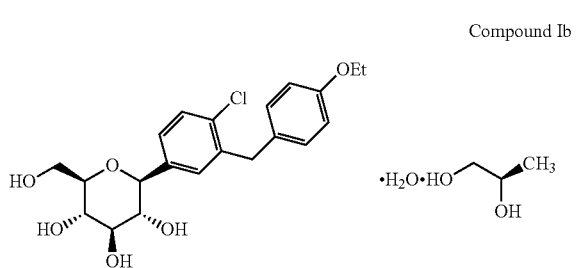

the preparation for which is disclosed in U.S. application Ser. No. 11/765,481, filed Jun. 28, 2007, U.S. Publication No. 2008-0004336 A1, and Provisional Application No. 60/817,118, filed Jun. 28, 2006, the disclosures of both of which are incorporated herein by reference in their entireties.

In one embodiment of the invention, the immediate release pharmaceutical formulation of the invention is in the form of a stock granulation (e.g., granules, beads, and/or beadlets), for loading in capsules or forming into tablets, comprising
   a) dapagliflozin or dapagliflozin propylene glycol hydrate;
   b) one or more bulking agents;
   c) optionally one or more binders;
   d) optionally one or more disintegrants;
   e) optionally one or more glidants and/or anti-adherents; and
   f) optionally one or more lubricants.

In one embodiment, the stock granulation comprises dapagliflozin and one or more bulking agents. In another embodiment, the stock granulation comprises dapagliflozin propylene glycol hydrate and one or more bulking agents. Suitable bulking agents include, for example, microcrystalline cellulose and/or lactose, as well as others provided herein and known in the art. In other embodiments, the stock granulation optionally comprises one or more of the following compounds: (1) one or more binders; (2) one or more disintegrants; (3) one or more glidants and/or anti-adherents; and (4) one or more lubricants. Suitable binders include, for example, pregelatinized starch, as well as others provided herein and known in the art. Suitable disintegrants include, for example, sodium starch glycolate, crospovidone, and croscarmellose sodium, as well as others provided herein and known in the art. Suitable glidants and/or anti-adherents include, for example, silicon dioxide and talc, as well as others provided herein and known in the art. Suitable lubricants include, for example, magnesium stearate, as well as others provided herein and known in the art.

The stock granulation of the invention as described above, and capsules and tablets containing same, is prepared by mixing together dapagliflozin or dapagliflozin propylene glycol and one or more bulking agents, in any desired order, to form the stock granulation; and filling the capsules with or forming tablets from desired quantities of the stock granulation. In other embodiments, the stock granulation of the invention is prepared by mixing together dapagliflozin or dapagliflozin propylene glycol hydrate and one or more bulking agents; and optionally one or more of the following compounds: binder(s); disintegrant(s); glidant(s) and/or anti-adherent(s); and lubricant(s) in any desired order, to form the stock granulation and filling the capsules with or forming tablets from desired quantities of stock granulation.

The tablets of the invention as described above are prepared by compressing the stock granulation into tablet form. In one embodiment, the tablets of the invention are prepared by compressing the stock granulation having one or more binder(s). In another embodiment, the tablets of the invention are prepared by compressing the stock granulation containing one or more anti-adherent(s) and/or glidant(s). In other embodiments, the tablets of the invention are prepared by compressing the stock granulation comprising one or more of the following compounds: (1) one or more binders; (2) one or more disintegrants; (3) one or more glidants and/or anti-adherents; and (4) one or more lubricants.

Optionally, the tablets and/or capsules of the invention can include an outer protective coating which comprises a coating polymer, such as, for example, polyvinyl alcohol (PVA), hydroxypropyl methyl cellulose, and hydroxypropyl cellulose, and/or a plasticizer(s) and optional colorant(s). Other optional components of the outer protective coating include anti-adherent(s) and/or glidant(s) and opacifying agent(s).

The pharmaceutical dapagliflozin and dapagliflozin propylene glycol hydrate formulations of the invention including the stock granulation, capsules containing same, and tablets of the invention are useful in the treatment of mammals, such as humans, dogs, and cats, for diseases or disorders associated with SGLT2 activity. Thus, the invention provides pharmaceutical dapagliflozin formulations and dapagliflozin propylene glycol hydrate formulations for use in the treatment of diseases or disorders associated with SGLT2 activity, for example, Type I and Type II diabetes; impaired glucose tolerance; insulin resistance; and diabetic complications, such as nephropathy, retinopathy, neuropathy and cataracts; hyperglycemia; hyperinsulinemia; hypercholesterolemia; dyslipidemia; elevated blood levels of free fatty acids or glycerol; hyperlipidemia; hypertriglyceridemia; obesity; wound healing; tissue ischemia; atherosclerosis; hypertension; and Syndrome X or Metabolic Syndrome.

In one embodiment, the invention provides the pharmaceutical formulation of the invention for use in the treatment of type II diabetes. In another embodiment, the invention provides the pharmaceutical formulation of the invention for use in delaying the progression or onset of type II diabetes.

The invention further provides a method for treating or delaying the progression or onset of diseases or disorders associated with SGLT2 activity comprising administering to a mammalian species in need of such treatment a therapeutically effective amount of a pharmaceutical formulation of the invention. In one embodiment, the invention provides a method for treating type II diabetes comprising administering to a mammalian species in need of such treatment a therapeutically effective amount of a pharmaceutical formulation of the invention. In one embodiment, the invention provides a method for delaying the progression or onset of type II diabetes comprising administering to a mammalian species in need of such treatment a therapeutically effective amount of a pharmaceutical formulation of the invention.

Other therapeutic agent(s) suitable for combination with the formulations of the present invention include, but are not limited to, known therapeutic agents useful in the treatment of the aforementioned disorders associated with SGLT2 activity including: anti-diabetic agents; anti-hyperglycemic agents; hypolipidemic or lipid lowering agents; anti-obesity agents; anti-hypertensive agents and appetite suppressants.

The invention further provides a method for treating or delaying the progression or onset of diseases or disorders associated with SGLT2 activity comprising administering to a mammalian species in need of such treatment a therapeutically effective amount of a pharmaceutical formulation of the invention and one or more of the following: an anti-diabetic agent(s), anti-hyperglycemic agent(s); hypolipidemic or lipid lowering agent(s); anti-obesity agent(s); anti-hypertensive agent(s) and appetite suppressant(s).

In one embodiment, the invention provides a method for treating type II diabetes comprising administering to a mammalian species in need of such treatment a therapeutically effective amount of a pharmaceutical formulation of the invention and one or more anti-diabetic agent(s). In one embodiment, the invention provides a method for delaying the progression or onset of type II diabetes comprising administering to a mammalian species in need of such treatment a therapeutically effective amount of a pharmaceutical formulation of the invention and one or more anti-diabetic agent(s). In one embodiment, the invention provides a method for treating or delaying the progression or onset of type II diabetes comprising administering to a mammalian species in need of such treatment a therapeutically effective amount of a pharmaceutical formulation of the invention and one or more of the following: an anti-hyperglycemic agent(s); hypolipidemic or lipid lowering agent(s); anti-obesity agent(s); anti-hypertensive agent(s) and appetite suppressant(s).

DETAILED DESCRIPTION OF THE INVENTION

The invention provides immediate release pharmaceutical formulations, which include, among others, tablet and capsule formulations, containing the sodium dependent glucose transporter (SGLT2) inhibitor dapagliflozin or its propylene glycol hydrate.

As used herein, the term "dapagliflozin" is intended to mean the structure shown as structure I or Compound I. The term "dapagliflozin propylene glycol hydrate" is meant to refer to and encompass both dapagliflozin (S)-propylene glycol hydrate (structure Ia or Compound Ia) and dapagliflozin (R)-propylene glycol hydrate (structure Ib or Compound Ib). As used herein, the terms "pharmaceutical formulation", "pharmaceutical formulation of the invention", and "formulation" are meant to refer to formulations containing dapagliflozin as well as formulations containing dapagliflozin propylene glycol hydrate. Likewise, the term "medicament" is meant in the present application to refer to dapagliflozin and dapagliflozin propylene glycol hydrate.

As used herein, the terms "immediate release" and "immediate release pharmaceutical formulation" are intended to mean that the pharmaceutical formulations of the invention are not produced using excipients that interfere with absorption of the active pharmaceutical ingredient, for example, dapagliflozin or dapagliflozin propylene glycol hydrate, when administered to a mammal or human.

The pharmaceutical formulation of the invention can be in the form of a capsule, tablet, bead, beadlet, granule or pill, all of the above being collectively referred to as pharmaceutical formulations, and contains medicament, namely dapagliflozin or dapagliflozin propylene glycol hydrate. In one embodiment, the medicament is dapagliflozin. In one embodiment, the medicament is dapagliflozin (S)-propylene glycol hydrate. In another embodiment, the medicament is dapagliflozin (R)-propylene glycol hydrate. In one embodiment of the invention, the immediate release pharmaceutical formulation of the invention is in the form of a stock granulation (e.g., granules, beads, and/or beadlets), for loading in capsules or forming into tablets.

In one embodiment, the dapagliflozin or dapagliflozin propylene glycol hydrate is in an amount within the range of from about 0.1% to about 70% by weight of the stock granulation and preferably in an amount within the range of from about 0.1% to about 30% by weight of the stock granulation.

The pharmaceutical formulation of the invention can include pharmaceutical excipients as described herein to aid in the formation of a stock granulation suitable in the form of granules, beads, or beadlets for capsule loading and for tablets of the invention. In one embodiment, the pharmaceutical formulation is in the form of a capsule or tablet containing a stock granulation comprising a) dapagliflozin or dapagliflozin propylene glycol hydrate;
b) at least one bulking agent or filler;
c) optionally at least one binder;
d) optionally at least one disintegrant;
e) optionally at least one glidant and/or anti-adherent; and
f) optionally at least one lubricant.

In the described embodiments of the pharmaceutical formulations of the invention, the amounts of medicament (dapagliflozin or dapagliflozin propylene glycol hydrate) and each of the excipient(s) are expressed as a percentage weight of the total weight of the stock granulation, which is equivalent in measurement to the percentage weight of the total weight of the tablet or capsule fill.

In one embodiment, the dapagliflozin or dapagliflozin propylene glycol hydrate is in an amount within the range of from about 0.1% to about 70% by weight of the stock granulation. In another embodiment, the dapagliflozin or dapagliflozin propylene glycol hydrate is in an amount within the range of from about 0.1% to about 30% by weight of the stock granulation.

In one embodiment, the bulking agent or filler is present in an amount within the range of from about 1% to about 95% by weight of the stock granulation. In another embodiment, the bulking agent or filler is present in an amount within the range of from about 10% to about 85% by weight of the stock granulation.

In one embodiment, the binder, if present, is present in an amount within the range of from about 0% to about 20% by weight of the stock granulation. In another embodiment, the binder, if present, is present in an amount within the range of from about 1% to about 10% by weight of the stock granulation. In another embodiment, the binder, if present, is present in an amount within the range of from about 2% to about 4% by weight of the stock granulation.

In one embodiment, the disintegrant, if present, is present in an amount within the range of from about 0% to about 20% by weight of the stock granulation. In another embodiment, the disintegrant, if present, is present in an amount within the range of from about 0.25% to about 10% by weight of the stock granulation.

In one embodiment, the glidant and/or anti-adherent, if present, is present in an amount within the range of from about 0% to about 20% by weight of the stock granulation. In another embodiment, the glidant and/or anti-adherent, if present, is present in an amount within the range of from about 1% to about 15% by weight of the stock granulation.

In one embodiment, the lubricant, if present, is present in an amount within the range of from about 0% to about 5% by weight of the stock granulation. In another embodiment, the lubricant, if present, is present in an amount within the range of from about 0.1% to about 5% by weight of the stock granulation. In another embodiment, the lubricant, if present, is present in an amount within the range of from about 0.2% to about 2% by weight of the stock granulation.

In one embodiment, the pharmaceutical formulation is in the form of a capsule or tablet containing a stock granulation comprising
  a) dapagliflozin or dapagliflozin propylene glycol hydrate;
  b) at least one bulking agent or filler;
  c) optionally at least one binder;
  d) optionally at least one disintegrant;
  e) optionally at least one glidant and/or anti-adherent; and
  f) optionally at least one lubricant.
wherein
  a) the dapagliflozin or dapagliflozin propylene glycol hydrate is present in an amount within the range of from about 0.1% to about 70% by weight;
  b) the bulking agent or filler is present in an amount within the range of from about 1% to about 95% by weight;
  c) the binder, if present, is present in an amount within the range of from about 0% to about 20% by weight;
  d) the disintegrant, if present, is present in an amount within the range of from about 0% to about 20% by weight;
  e) the glidant and/or anti-adherent, if present, is present in an amount within the range of from about 0% to about 20% by weight; and
  f) the lubricant, if present, is present in an amount within the range of from about 0% to about 5% by weight, all of the above % by weight being based on the weight of the stock granulation.

In one embodiment, the pharmaceutical formulation is in the form of a capsule or tablet containing a stock granulation comprising
  a) dapagliflozin or dapagliflozin propylene glycol hydrate;
  b) at least one bulking agent or filler;
  c) optionally at least one binder;
  d) optionally at least one disintegrant;
  e) optionally at least one glidant and/or anti-adherent; and
  f) optionally at least one lubricant.
wherein
  a) the dapagliflozin or dapagliflozin propylene glycol hydrate is present in an amount within the range of from about 0.1% to about 30% by weight
  b) the bulking agent or filler is present in an amount within the range of from about 10% to about 85% by weight;
  c) the binder, if present, is present in an amount within the range of from about 1% to about 10% by weight;
  d) the disintegrant, if present, is in an amount within the range of from about 0.25% to about 10% by weight;
  e) the glidant and/or anti-adherent, if present, is in an amount within the range of from about 1% to about 15% by weight; and
  f) the lubricant, if present, is in an amount within the range of from about 0.2% to about 2% by weight, all of the above % by weight being based on the weight of the stock granulation.

In one embodiment, the medicament in the pharmaceutical formulations has 90% of the particles smaller than 200 micrometers. In another embodiment, the medicament has 90% of its particles smaller than 100 micrometers. In another embodiment, the medicament has 90% of its particles smaller than 50 micrometers. Dapagliflozin or dapagliflozin propylene glycol hydrate can be milled or micronized as needed to obtain the above mentioned characteristics.

Examples of bulking agents or fillers suitable for use herein include, but are not limited to, cellulose derivatives, such as microcrystalline cellulose or wood cellulose, lactose, sucrose, starch, pregelatinized starch, dextrose, mannitol, fructose, xylitol, sorbitol, corn starch, modified corn starch, inorganic salts such as calcium carbonate, calcium phosphate, dicalcium phosphate, calcium sulfate, dextrin/dextrates, maltodextrin, compressible sugars, and other known bulking agents or fillers, and/or mixtures of two or more thereof. Several types of microcrystalline cellulose are suitable for use in the formulations described herein, for example, microcrystalline cellulose selected from the group consisting of Avicel® types: PH101, PH102, PH103, PH105, PH 112, PH113, PH200, PH301, and other types of microcrystalline cellulose, such as silicified microcrystalline cellulose. Several types of lactose are suitable for use in the formulations described herein, for example, lactose selected from the group consisting of anhydrous lactose, lactose monohydrate, lactose fast flo, directly compressible anhydrous lactose, and modified lactose monohydrate. In one embodiment of the invention, the bulking agent of the stock granulation is microcrystalline cellulose and/or lactose. Lactose is particularly useful for tablet formulation.

Examples of binders suitable for use herein include, but are not limited to, hydroxypropyl cellulose, corn starch, pregelatinized starch, modified corn starch, polyvinyl pyrrolidone (PVP) (typical molecular weight ranging from about 5,000 to about 1,000,000, preferably about 40,000 to 50,000), hydroxypropyl methylcellulose (HPMC), lactose, gum acacia, ethyl cellulose, cellulose acetate, as well as a wax binder such as carnauba wax, paraffin, spermaceti, polyethylenes or microcrystalline wax, as well as other conventional binding agents and/or mixtures of two or more thereof. In one embodiment of the invention, the binding agent, if present, of the stock granulation is pregelatinized starch.

Examples of disintegrants suitable for use herein include, but are not limited to, croscarmellose sodium, crospovidone, starch, potato starch, pregelatinized starch, corn starch, sodium starch glycolate, microcrystalline cellulose, low substituted hydroxypropyl cellulose and other known disintegrants. Several specific types of disintegrant are suitable for use in the formulations described herein. For example, any grade of crospovidone can be used, including for example crospovidone XL-10, and includes members selected from the group consisting of Kollidon CL®, Polyplasdone XL®, Kollidon CL-M®, Polyplasdone XL-10®, and Polyplasdone INF-10®. In one embodiment, the disintegrant, if present, of the stock granulation is sodium starch glycolate, croscarmellose sodium and/or crospovidone. In one embodiment, the disintegrant is sodium starch glycolate. In another embodiment, the disintegrant is croscarmellose sodium and/or crospovidone, which are particularly useful for tablet formulation. In one specific embodiment, the disintegrant is crospovidone XL-10 with peroxide levels below 400 parts per million (ppm). These materials are also referred to as insoluble polyvidone, insoluble PVP, crosslinked PVP, and PVPP. The crospovidone can be substituted with croscarmellose sodium, sodium starch glycolate, or pregelatinized starch (at, for example, a 5-10% concentration).

Examples of lubricants suitable for use herein include, but are not limited to, magnesium stearate, zinc stearate, calcium stearate, talc, carnauba wax, stearic acid, palmitic acid, sodium stearyl fumarate sodium laurel sulfate, glyceryl palmitostearate, palmitic acid, myristic acid and hydrogenated vegetable oils and fats, as well as other known lubricants, and/or mixtures of two or more thereof. In one embodiment, the lubricant, if present, of the stock granulation is magnesium stearate.

Examples of glidants and/or anti-adherents suitable for use herein include but are not limited to, silicon dioxide (generally), colloidal silicon dioxide, magnesium silicate, magnesium trisilicate, talc, and other forms of silicon dioxide, such as aggregated silicates and hydrated silica.

In one embodiment of the stock granulation, the bulking agent is microcrystalline cellulose and/or lactose monohydrate, the binder, if present, is pregelatinized starch, the disintegrant, if present, is sodium starch glycolate, croscarmellose sodium and/or crospovidone, the lubricant, if present, is magnesium stearate and the glidant and/or anti-adherent, if present, is silicon dioxide and/or talc.

In one embodiment, the tablet or capsule has a protective outer layer. The protective outer layer of the tablet or capsule, where present, can include from about 10% to about 95% of polymer based on the weight of the coating layer, and can be prepared employing conventional procedures. In one embodiment, the outer layer of the tablet or capsule includes from about 20% to about 90% of polymer based on the weight of the coating layer. The formulation can contain at least one coating layer polymer and a coating solvent, for example, water, which is used for processing and removed by drying. Suitable examples of polymer for the coating layer include, but are not limited to, hydroxypropyl methylcellulose, polyvinyl alcohol (PVA), ethyl cellulose, methacrylic polymers, hydroxypropyl cellulose, and starch. In one embodiment, the coating layer polymer is PVA. In another embodiment, the coating layer polymer is hydroxypropyl cellulose. Use of PVA allows for enhanced logo definition, film adhesion, and facilitates faster coating of the drug, the latter of which can be important for dapagliflozin formulations due to the temperature sensitivity of the compound.

The coating can also optionally include a plasticizer of from about 0% to about 30% by weight, based on the weight of the coating layer. In one embodiment, the plasticizer is from about 15% to about 25% by weight of the coating layer. Suitable platicizers include, but are not limited to, triacetin, diethyl phthalate, tributyl sebacate, polyethylene glycol (PEG), glycerin, triacetin, and triaethyl citrate, for example. In one embodiment, the platicizer is polyethylene glycol of molecular weight 200 to 20,000. In another embodiment, the platicizer is polyethylene glycol of molecular weight 400 to 4,000. In another embodiment, the platicizer is polyethylene glycol of molecular weight 400.

In another embodiment, the coating can also optionally include an anti-adherent or glidant such as talc, fumed silica, or magnesium stearate, for example. In another embodiment, the coating can also optionally include an opacifying agent, such as titanium dioxide, for example. In yet another embodiment, the coating layer can also optionally include one or more colorants, for example, iron oxide based colorant(s).

Examples of commercially available coating material include Opadry® HP and Opadry® II white.

The pharmaceutical formulations disclosed herein can further comprise antioxidants and chelating agents. For example, the pharmaceutical formulations can comprise butylated hydroxyanisole (BHA), butylated hydroxytoluene (BHT), propyl gallate (PG), sodium metabisulfite, ascorbyl palmitate, potassium metabisulfite, disodium EDTA (ethylenediamine tetraacetic acid; also known as disodium edentate), EDTA, tartaric acid, citric acid, citric acid monohydrate, and sodium sulfite. In one embodiment, the foregoing compounds are included in the pharmaceutical formulations in amounts in the range of about 0.01% to about 5% w/w. In one specific embodiment, the pharmaceutical formulation includes BHA, BHT, or PG used at a range of about 0.02% to about 1% and disodium EDTA, citric acid, or citric acid monohydrate used at a range of about 2% to about 5%. In a preferred embodiment, the pharmaceutical formulation includes BHA used at about 0.05% w/w.

The pharmaceutical formulations of the invention as described above are prepared by mixing together dapagliflozin or dapagliflozin propylene glycol hydrate and one or more of the desired excipients described herein in any desired order, to form the stock granulation; and filling the capsules with or forming tablets from desired quantities of the stock granulation. The stock granulation, capsules and tablets of the invention can be prepared by a variety of processes and order of addition of excipients. The utility of these formulations is not limited to a specific dosage form or manufacturing process. For example, stock formulation tablets can be manufactured by wet granulation, dry granulation, direct blending or any other pharmaceutically acceptable process described herein or otherwise known in the art.

The pharmaceutical formulations of the invention can be packaged in any packaging that facilitates stability of the drug formulation. For example, sealed high density polyethylene (HDPE) bottles containing silica gel desiccant or aluminum blister lined with PVC can be used. Use of such packaging helps to control unwanted oxidation of the product at room temperature.

Examples of certain specific embodiments of tablet and capsule formulations in accordance with the invention are set out below.

TABLE I

Tablet and Capsule Formulations

| Material | Possible Range % by weight of tablet or capsule fill | Preferred Range % by weight of tablet or capsule fill |
|---|---|---|
| Dapagliflozin or Dapagliflozin propylene glycol hydrate | 0.1 to 70% | 0.1 to 30% |
| Bulking Agent/binder | 1 to 95% | 10 to 85% |
| Anhydrous Lactose | 0 to 95% | 20 to 75% |
| Micro crystalline cellulose | 0 to 95% | 20 to 75% |
| Pregelatinized starch | 0 to 95% | 10 to 75% |
| Disintegrant | 0 to 20% | 0.25 to 10% |
| Croscarmellose sodium | 0 to 20% | 2 to 10% |
| Crospovidone | 0 to 12% | 4 to 10% |
| Sodium Starch glycolate | 0 to 20% | 2 to 10% |
| Lubricant | 0.1 to 5% | 0.2 to 2% |
| Magnesium Stearate | 0.1 to 5% | 0.2 to 2% |
| Anti adherent/glidant | 0 to 10% | 1 to 10% |
| Talc, silicon dioxide | | more preferably 1 to 4% |

TABLE I-continued

Tablet and Capsule Formulations

| Outer Protective Coating Layer | % by weight of tablet or capsule fill | % by weight of tablet or capsule fill |
|---|---|---|
| Coating polymer, and optional plasticizer(s), glidant(s), anti-tacking agent(s), and colorant(s) | 0.5 to 50% | 1 to 5% |

TABLE II

Granulation Composition (% w/w) for Tablets and Capsules

| Ingredient | Possible Range % by weight | Preferred range % by weight |
|---|---|---|
| Dapagliflozin or Dapagliflozin Propylene Glycol Hydrate | 0.1-40 | 0.1-10 |
| Microcrystalline Cellulose | q.s. | q.s. |
| Anhydrous Lactose | 0-50 | 10-30 |
| Crospovidone | 1-15 | 3-10 |
| Silicon Dioxide | 0-6 | 0.5-4 |
| Magnesium Stearate | 0.0-4.0 | 0.5-2.0 | q.s. refers to the quantity sufficient to make the granulation composition 100% w/w.

A film coating for capsules or tablets of Table II comprises, for example, polyvinyl alcohol (PVA), titanium dioxide, polyethylene glycol, talc, and colorant.

Tablets or capsules of various strengths (0.1-50 mg) can be prepared using different weights of the stock granulations described herein.

The pharmaceutical formulation in the form of a tablet can be obtained by a process comprising the steps of:

a) mixing the inactive ingredients with the medicament (Dapagliflozin or Dapagliflozin propylene glycol hydrate) using a combination of blending and milling processes;
b) formulating granules;
c) drying and/or screening the granules;
d) blending the granules; and
e) tabletting the blend obtained in (d) into tablets.

In one embodiment, step a) of the process employs impact milling and/or sizing equipment. In one embodiment, the granules in step b) of the process are formulated by dry granulation, wet granulation, or direct compression. In one embodiment, the granules are formulated by dry granulation. In one embodiment, the granules in step d) of the process are blended with a tableting aid or a lubricant and filler.

The pharmaceutical formulation in the form of a capsule can be obtained by a process comprising the steps of:

a) mixing the inactive ingredients with the medicament using a combination of blending and milling processes;
b) formulating granules;
c) drying and/or screening the granules; and
(d) loading the granules into capsules.

In one embodiment, step a) of the process employs impact milling and/or sizing equipment. In one embodiment, the granules in step b) of the process are formulated by dry granulation, wet granulation, or direct compression. In one embodiment, the granules are formulated by dry granulation.

The dapagliflozin propylene glycol hydrate ((S) form and (R) form) can be prepared, for example, by a process as described in U.S. application Ser. No. 11/765,481, filed Jun. 28, 2007, U.S. Publication No. 2008-0004336 A1, and provisional application No. 60/817,118 filed Jun. 28, 2006.

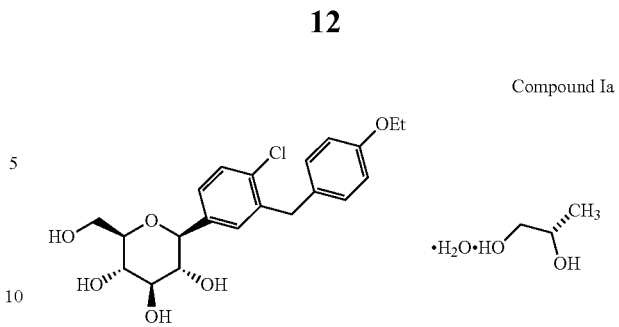

Compound Ia

For example, dapagliflozin (S)-propylene glycol hydrate (Compound Ia) can be prepared by the following steps: providing a compound A (prepared as described in U.S. application Ser. No. 10/745,075 filed Dec. 23, 2003, Examples 17 to 20), of the structure (A):

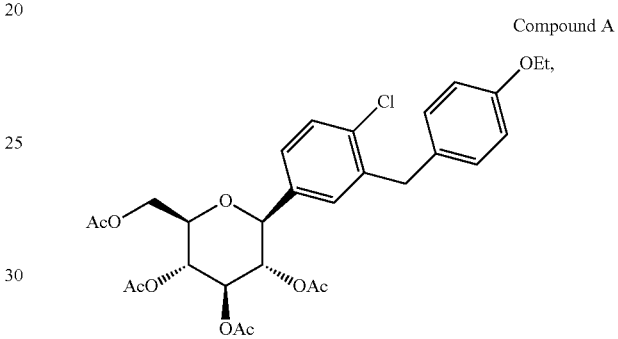

Compound A treating compound A with an alcohol solvent, such as methanol or ethanol, and aqueous base, such as sodium hydroxide, and water, if necessary, under an inert atmosphere, and elevated temperature, if necessary; adding an acid, such as hydrochloric acid to neutralize the reaction mixture, to form compound I of the structure;

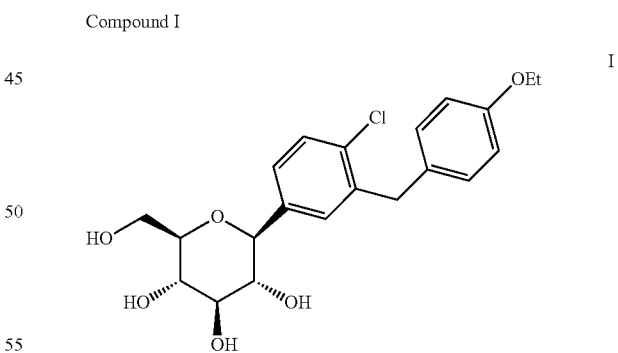

Compound I treating the reaction mixture containing compound I with an organic solvent, such as methyl t-butyl ether, an alkyl acetate, such as ethyl acetate, methyl acetate, isopropyl acetate, or butyl acetate, and (S)-propylene glycol; optionally adding seeds of (S)-propylene glycol compound Ia (SC-3) to the mixture, to form dapagliflozin (S)-propylene glycol compound Ia (SC-3 form).

In another example, dapagliflozin propylene glycol hydrate can be prepared in a process comprising the step of reducing a compound of the structure (B)

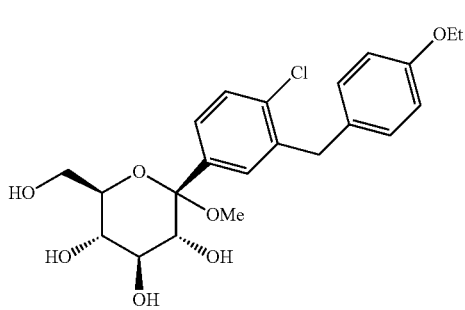

to remove the methoxy group; treating compound B with a reducing agent, such as triethylsilyl hydride and an activating group which is a Lewis acid, such as $BF_3 \cdot Et_2O$, and an organic solvent, such as $CH_3CN$, and water; separating out the compound of the structure (I);

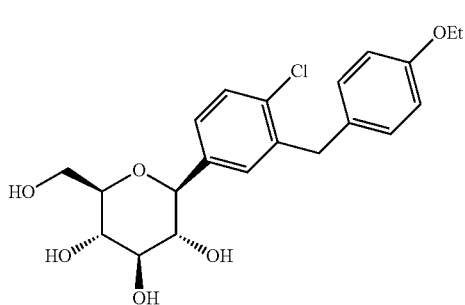

and treating compound I with (S)-propylene glycol in the presence of a solvent, such as t-butylmethyl ether, and optionally with seeds of compound Ia (dapagliflozin (S)-propylene glycol), to form a crystal slurry of compound Ia (dapagliflozin (S)-propylene glycol) and separating out compound Ia (dapagliflozin (S)-propylene glycol).

The above process of the invention is a one-pot operation which minimizes the production of intermediates, resulting in improved yield and priority of the final crystalline compound Ia dapagliflozin(S)-propylene glycol.

In carrying out the formation of compound Ia, the (S)-propylene glycol is employed in a molar ratio to compound I with the range of from about 0.9:1 to about 1.5:1. In one embodiment, the (S)-propylene glycol is employed in a molar ratio to compound I with the range of from about 0.98:1 to about 1.2:1.

Dapagliflozin (R)-propylene glycol hydrate (Compound Ib) can be prepared by the following steps: providing a compound A (prepared as described in U.S. application Ser. No. 10/745,075 filed Dec. 23, 2003, Examples 17 to 20), of the structure (A);

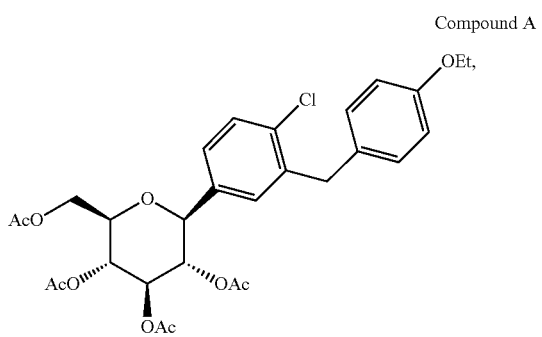 [SMILES: CCOc1ccc(Cc2cc([C@@H]3O[C@H](COC(C)=O)[C@@H](OC(C)=O)[C@H](OC(C)=O)[C@H]3OC(C)=O)ccc2Cl)cc1]

treating compound A with an alcohol solvent, such as methanol or ethanol, and aqueous base, such as sodium hydroxide, and water, if necessary, under an inert atmosphere, and elevated temperature, if necessary; adding an acid, such as hydrochloric acid to neutralize the reaction mixture, to form compound I of the structure;

Compound I

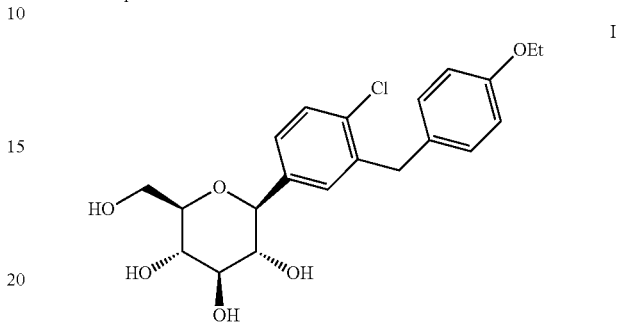

treating the reaction mixture containing compound I with an organic solvent, such as methyl t-butyl ether, an alkyl acetate, such as ethyl acetate, methyl acetate, isopropyl acetate, or butyl acetate, and (R)-propylene glycol; optionally adding seeds of (R)-propylene glycol Compound Ib (SD-3) to the mixture, to form dapagliflozin (R)-propylene glycol Compound Ib (SD-3 form).

Compound Ib (SD-3)

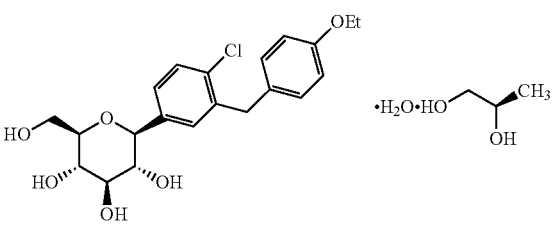

The activity of dapagliflozin or dapagliflozin propylene glycol hydrate can be determined using, for example, the assay system described below or any appropriate assay system known in the art.

The mRNA sequence for human SGLT2 (GenBank #M95549) is cloned by reverse-transcription and amplification from human kidney mRNA, using standard molecular biology techniques. The cDNA sequence is stably transfected into CHO cells, and clones are assayed for SGLT2 activity essentially as described in Ryan et al., "HK-2: an immortalized proximal tubule epithelial cell line from normal adult human kidney", Kidney International, 45:48-57 (1994). Evaluation of inhibition of SGLT2 activity in a clonally selected cell line is performed essentially as described in Ryan et al. (1994), with the following modifications. Cells are grown in 96-well plates for 2-4 days to 75,000 or 30,000 cells per well in F-12 nutrient mixture (Ham's F-12), 10% fetal bovine serum, 300 ug/ml Geneticin and penicillin-streptomycin. At confluence, the cells are washed twice with 10 mM Hepes/Tris, pH 7.4, 137 mM N-methyl-D-glucamine, 5.4 mM KCl, 2.8 mM $CaCl_2$, 1.2 mM $MgSO_4$. Cells are then incubated with 10 μM [$^{14}$C]AMG, and 10 μM inhibitor (final DMSO=0.5%) in 10 mM Hepes/Tris, pH 7.4, 137 mM NaCl, 5.4 mM KCl, 2.8 mM CaCl$_2$, 1.2 mM MgSO$_4$ at 37° C. for 1.5 hours. Uptake assays are quenched with ice cold 1×PBS containing 0.5 mM phlorizin, and cells are then lysed with 0.1% NaOH. After addition of MicroScint scintillation fluid, the cells are allowed to shake for 1 hour, and then [$^{14}$C]AMG (glucose analog α-methyl-D-glucopyranoside) is quantitated on a TopCount scintillation counter. Controls are performed with and without NaCl. For determination of EC$_{50}$ values, 10 inhibitor concentrations (dapagliflozin) are used over 2 log intervals in the appropriate response range, and triplicate plates are averaged across plates.

The pharmaceutical formulations of the present invention containing dapagliflozin or dapagliflozin propylene glycol hydrate possess activity as an inhibitor of the sodium dependent glucose transporters found in the intestine and kidney of mammals, is a selective inhibitor of renal SGLT2 activity, and therefore can be used in the treatment of diseases or disorders associated with SGLT2 activity.

Accordingly, the pharmaceutical dapagliflozin and dapagliflozin propylene glycol hydrate formulations of the present invention can be administered to mammals, preferably humans, for the treatment of a variety of conditions and disorders associated with SGLT2 activity including, but not limited to, treating or delaying the progression or onset of diabetes (including Type I and Type II diabetes, impaired glucose tolerance, insulin resistance, and diabetic complications, such as nephropathy, retinopathy, neuropathy and cataracts), hyperglycemia, hyperinsulinemia, hypercholesterolemia, dyslipidemia, elevated blood levels of free fatty acids or glycerol, hyperlipidemia, hypertriglyceridemia, obesity, wound healing, tissue ischemia, atherosclerosis and hypertension. The formulations of the present invention can also be utilized to increase the blood levels of high density lipoprotein (HDL). In addition, the conditions, diseases, and maladies collectively referenced to as "Syndrome X" or Metabolic Syndrome as detailed in Johannsson, *J. Clin. Endocrinol. Metab.*, 82, 727-34 (1997), can be treated employing the formulations of the present invention.

In one embodiment, the invention provides the pharmaceutical dapagliflozin and dapagliflozin propylene glycol hydrate formulations of the invention for use in the treatment of type II diabetes. In another embodiment, the invention provides the pharmaceutical dapagliflozin and dapagliflozin propylene glycol hydrate formulations of the invention for use in delaying the progression or onset of type II diabetes.

The invention further provides a method for treating or delaying the progression or onset of diseases or disorders associated with SGLT2 activity comprising administering to a mammalian species in need of such treatment a therapeutically effective amount of the pharmaceutical dapagliflozin or dapagliflozin propylene glycol hydrate formulation of the invention. In one embodiment, the invention provides a method for treating type II diabetes comprising administering to a mammalian species in need of such treatment a therapeutically effective amount of the pharmaceutical dapagliflozin or dapagliflozin propylene glycol hydrate formulation of the invention. In another embodiment, the invention provides a method for delaying the progression or onset of type II diabetes comprising administering to a mammalian species in need of such treatment a therapeutically effective amount of the pharmaceutical dapagliflozin or dapagliflozin propylene glycol hydrate formulation of the invention.

In one embodiment, the invention provides the use of the pharmaceutical dapagliflozin or dapagliflozin propylene glycol hydrate formulation of the invention (including the stock granulation, capsules containing same, and tablets thereof) in the manufacture of a medicament for the treatment of type II diabetes. In another embodiment, the invention provides the use of the pharmaceutical dapagliflozin or dapagliflozin propylene glycol hydrate formulation of the invention in the manufacture of a medicament for delaying the progression or onset of type II diabetes. The invention also provides the pharmaceutical dapagliflozin or dapagliflozin propylene glycol hydrate formulation of the invention for use in therapy in treating or delaying the progression or onset of type II diabetes.

Other therapeutic agent(s) suitable for combination with the formulations of the present invention include, but are not limited to, known therapeutic agents useful in the treatment of the aforementioned disorders associated with SGLT2 activity including: anti-diabetic agents; anti-hyperglycemic agents; hypolipidemic or lipid lowering agents; anti-obesity agents; anti-hypertensive agents and appetite suppressants.

The invention further provides a method for treating or delaying the progression or onset of diseases or disorders associated with SGLT2 activity comprising administering to a mammalian species in need of such treatment a therapeutically effective amount of the pharmaceutical formulation of the invention and one or more of the following: anti-diabetic agent(s), anti-hyperglycemic agent(s); hypolipidemic or lipid lowering agent(s); anti-obesity agent(s); anti-hypertensive agent(s) and appetite suppressant(s).

In one embodiment, the invention provides a method for treating type II diabetes comprising administering to a mammalian species in need of such treatment a therapeutically effective amount of the pharmaceutical formulation of the invention and one or more anti-diabetic agent(s). In another embodiment, the invention provides a method for delaying the progression or onset of type II diabetes comprising administering to a mammalian species in need of such treatment a therapeutically effective amount of the pharmaceutical formulation of the invention and one or more anti-diabetic agent(s).

In another embodiment, the invention provides a method for treating or delaying the progression or onset of type II diabetes comprising administering to a mammalian species in need of such treatment a therapeutically effective amount of the pharmaceutical formulation of the invention and one or more of the following: anti-hyperglycemic agent(s); hypolipidemic or lipid lowering agent(s); anti-obesity agent(s); anti-hypertensive agent(s) and appetite suppressant(s). For example, the invention provides a method for treating or delaying the progression or onset of type II diabetes comprising administering to a mammalian species in need of such treatment a therapeutically effective amount of a pharmaceutical formulation of the invention and an anti-hyperglycemic agent(s). In another embodiment, the invention provides a method for treating or delaying the progression or onset of type II diabetes comprising administering to a mammalian species in need of such treatment a therapeutically effective amount of a pharmaceutical formulation of the invention and a hypolipidemic agent(s). In another embodiment, the invention provides a method for treating or delaying the progression or onset of type II diabetes comprising administering to a mammalian species in need of such treatment a therapeutically effective amount of a pharmaceutical formulation of the invention and an anti-obesity agent(s). In another embodiment, the invention provides a method for treating or delaying the progression or onset of type II diabetes comprising administering to a mammalian species in need of such treatment a therapeutically effective amount of a pharmaceutical formulation of the invention and an anti-hypertensive agent(s). In another embodiment, the invention provides a method for treating or delaying the progression or onset of type II diabetes comprising administering to a mammalian species in need of such treatment a therapeutically effective amount of a pharmaceutical formulation of the invention and an appetite suppressant(s).

The invention provides the use of the pharmaceutical dapagliflozin or dapagliflozin propylene glycol hydrate formulations of the invention (including the stock granulation, capsules containing same, and tablets thereof) in the manufacture of a medicament for the treatment of diseases or disorders associated with SGLT2 activity, for example, Type I and Type II diabetes; impaired glucose tolerance; insulin resistance; and diabetic complications, such as nephropathy, retinopathy, neuropathy and cataracts; hyperglycemia; hyperinsulinemia; hypercholesterolemia; dyslipidemia; elevated blood levels of free fatty acids or glycerol; hyperlipidemia; hypertriglyceridemia; obesity; wound healing; tissue ischemia; atherosclerosis; hypertension; and Syndrome X or Metabolic Syndrome.

The invention provides the use of the combination of the pharmaceutical dapagliflozin or dapagliflozin propylene glycol hydrate formulations of the invention and one or more agents selected from the group consisting of anti-diabetic agents, anti-hyperglycemic agents, hypolipidemic or lipid lowering agents, anti-obesity agents, anti-hypertensive agents, and appetite suppressants as a medicament for the treatment of diseases or disorders associated with SGLT2 activity, for example, Type I and Type II diabetes; impaired glucose tolerance; insulin resistance; and diabetic complications, such as nephropathy, retinopathy, neuropathy and cataracts; hyperglycemia; hyperinsulinemia; hypercholesterolemia; dyslipidemia; elevated blood levels of free fatty acids or glycerol; hyperlipidemia; hypertriglyceridemia; obesity; wound healing; tissue ischemia; atherosclerosis; hypertension; and Syndrome X or Metabolic Syndrome.

In one embodiment, the invention provides the combination of the pharmaceutical dapagliflozin or dapagliflozin propylene glycol hydrate formulation of the invention and one or more anti-diabetic agents as a medicament for the treatment of type II diabetes. In another embodiment, the invention provides the combination of the pharmaceutical dapagliflozin or dapagliflozin propylene glycol hydrate formulation of the invention and one or more anti-diabetic agents as a medicament for delaying the progression or onset of type II diabetes. In another embodiment, the invention provides the combination of the pharmaceutical dapagliflozin or dapagliflozin propylene glycol hydrate formulation of the invention and one or more anti-hyperglycemic agents as a medicament for the treatment of type II diabetes. In another embodiment, the invention provides the combination of the pharmaceutical dapagliflozin or dapagliflozin propylene glycol hydrate formulation of the invention and one or more anti-hyperglycemic agents as a medicament for delaying the progression or onset of type II diabetes. In another embodiment, the invention provides the combination of the pharmaceutical dapagliflozin or dapagliflozin propylene glycol hydrate formulation of the invention and one or more hypolipidemic agents or lipid-lowering agents as a medicament for the treatment of type II diabetes. In another embodiment, the invention provides the combination of the pharmaceutical dapagliflozin or dapagliflozin propylene glycol hydrate formulation of the invention and one or more hypolipidemic agents or lipid-lowering agents as a medicament for delaying the progression or onset of type II diabetes. In another embodiment, the invention provides the combination of the pharmaceutical dapagliflozin or dapagliflozin propylene glycol hydrate formulation of the invention and one or more anti-obesity agents as a medicament for the treatment of type II diabetes. In another embodiment, the invention provides the combination of the pharmaceutical dapagliflozin or dapagliflozin propylene glycol hydrate formulation of the invention and one or more anti-obesity agents as a medicament for delaying the progression or onset of type II diabetes. In another embodiment, the invention provides the combination of the pharmaceutical dapagliflozin or dapagliflozin propylene glycol hydrate formulation of the invention and one or more anti-hypertensive agents as a medicament for the treatment of type II diabetes. In another embodiment, the invention provides the combination of the pharmaceutical dapagliflozin or dapagliflozin propylene glycol hydrate formulation of the invention and one or more anti-hypertensive agents as a medicament for delaying the progression or onset of type II diabetes. In another embodiment, the invention provides the combination of the pharmaceutical dapagliflozin or dapagliflozin propylene glycol hydrate formulation of the invention and one or more appetite suppressants as a medicament for the treatment of type II diabetes. In another embodiment, the invention provides the combination of the pharmaceutical dapagliflozin or dapagliflozin propylene glycol hydrate formulation of the invention and one or more appetite suppressants as a medicament for delaying the progression or onset of type II diabetes.

The invention provides the use of the pharmaceutical dapagliflozin or dapagliflozin propylene glycol hydrate formulation of the invention in the manufacture of a medicament for treating or delaying the progression or onset of Type I and Type II diabetes, impaired glucose tolerance, insulin resistance, nephropathy, retinopathy, neuropathy, cataracts, hyperglycemia, hyperinsulinemia, hypercholesterolemia, dyslipidemia, elevated blood levels of free fatty acids or glycerol, hyperlipidemia, hypertriglyceridemia, obesity, wound healing, tissue ischemia, atherosclerosis, hypertension, or Syndrome X (Metabolic Syndrome), in which such treatment comprises a combination with one or more agents selected from the group consisting of anti-diabetic agents, anti-hyperglycemic agents, hypolipidemic or lipid lowering agents, anti-obesity agents, anti-hypertensive agents, and appetite suppressants, for concurrent or sequential use, in any order.

In one embodiment, the invention provides the use of the pharmaceutical dapagliflozin or dapagliflozin propylene glycol hydrate formulation of the invention in the manufacture of a medicament for the treatment of type II diabetes, in which such treatment comprises a combination with one or more anti-diabetic agents, for concurrent or sequential use, in any order. In another embodiment, the invention provides the use of the pharmaceutical dapagliflozin or dapagliflozin propylene glycol hydrate formulation of the invention in the manufacture of a medicament for delaying the progression or onset of type II diabetes, in which such treatment comprises a combination with one or more anti-diabetic agents, for concurrent or sequential use, in any order. In another embodiment, the invention provides the use of the pharmaceutical dapagliflozin or dapagliflozin propylene glycol hydrate formulation of the invention in the manufacture of a medicament for the treatment of type II diabetes, in which such treatment comprises a combination with one or more anti-hyperglycemic agents, for concurrent or sequential use, in any order. In another embodiment, the invention provides the use of the pharmaceutical dapagliflozin or dapagliflozin propylene glycol hydrate formulation of the invention in the manufacture of a medicament for delaying the progression or onset of type II diabetes, in which such treatment comprises a combination with one or more anti-hyperglycemic agents, for concurrent or sequential use, in any order. In another embodiment, the invention provides the use of the pharmaceutical dapagliflozin or dapagliflozin propylene glycol hydrate formulation of the invention in the manufacture of a medicament for the treatment of type II diabetes, in which such treatment comprises a combination with one or more hypolipidemic agent or lipid-lowering agents, for concurrent or sequential use, in any order. In another embodiment, the invention provides the use of the pharmaceutical dapagliflozin or dapagliflozin propylene glycol hydrate formulation of the invention in the manufacture of a medicament for delaying the progression or onset of type II diabetes, in which such treatment comprises a combination with one or more hypolipidemic agents or lipid-lowering agents, for concurrent or sequential use, in any order. In another embodiment, the invention provides the use of the pharmaceutical dapagliflozin or dapagliflozin propylene glycol hydrate formulation of the invention in the manufacture of a medicament for the treatment of type II diabetes, in which such treatment comprises a combination with one or more anti-obesity agents, for concurrent or sequential use, in any order. In another embodiment, the invention provides the use of the pharmaceutical dapagliflozin or dapagliflozin propylene glycol hydrate formulation of the invention in the manufacture of a medicament for delaying the progression or onset of type II diabetes, in which such treatment comprises a combination with one or more anti-obesity agents, for concurrent or sequential use, in any order. In another embodiment, the invention provides the use of the pharmaceutical dapagliflozin or dapagliflozin propylene glycol hydrate formulation of the invention in the manufacture of a medicament for the treatment of type II diabetes, in which such treatment comprises a combination with one or more anti-hypertensive agents, for concurrent or sequential use, in any order. In another embodiment, the invention provides the use of the pharmaceutical dapagliflozin or dapagliflozin propylene glycol hydrate formulation of the invention in the manufacture of a medicament for delaying the progression or onset of type II diabetes, in which such treatment comprises a combination with one or more anti-hypertensive agents, for concurrent or sequential use, in any order. In another embodiment, the invention provides the use of the pharmaceutical dapagliflozin or dapagliflozin propylene glycol hydrate formulation of the invention in the manufacture of a medicament for the treatment of type II diabetes, in which such treatment comprises a combination with one or more appetite suppressants, for concurrent or sequential use, in any order. In another embodiment, the invention provides the use of the pharmaceutical dapagliflozin or dapagliflozin propylene glycol hydrate formulation of the invention in the manufacture of a medicament for delaying the progression or onset of type II diabetes, in which such treatment comprises a combination with one or more appetite suppressants, for concurrent or sequential use, in any order.

The formulations of the invention in the form of capsules or tablets containing dapagliflozin or dapagliflozin propylene glycol hydrate can be administered in dosages of about 0.1 mg to about 750 mg per day, in single or divided doses or multiple doses which can be administered 1 to 4 times daily. In one embodiment, the formulations of the invention in the form of capsules or tablets containing dapagliflozin or dapagliflozin propylene glycol hydrate is administered in dosages of about 0.2 mg to about 600 mg per day, in single or divided doses or multiple doses which can be administered 1 to 4 times daily. In another embodiment, the formulations of the invention in the form of capsules or tablets containing dapagliflozin or dapagliflozin propylene glycol hydrate is administered in dosages of from about 0.5 mg to about 100 mg per day, in single or divided doses or multiple doses which can be administered 1 to 4 times daily.

The present invention includes within its scope pharmaceutical formulations containing, as an active ingredient, a therapeutically effective amount of dapagliflozin or dapagliflozin propylene glycol hydrate, alone or in combination with a pharmaceutical carrier or diluent as described. Optionally, the formulations of the present invention can be utilized as an individual treatment, or utilized in combination with one or more other therapeutic agent(s) in the same dosage form (fixed dosage) or separate dosage forms.

Other therapeutic agent(s) suitable for combination with the formulations of the present invention include, but are not limited to, known therapeutic agents useful in the treatment of the aforementioned disorders including: anti-diabetic agents; anti-hyperglycemic agents; hypolipidemic/lipid lowering agents; anti-obesity agents; anti-hypertensive agents and appetite suppressants.

Examples of suitable anti-diabetic agents for use in combination with the formulations of the present invention include, but are not limited to, biguanides (e.g., metformin or phenformin), glucosidase inhibitors (e.g., acarbose or miglitol), insulins (including insulin secretagogues or insulin sensitizers), meglitinides (e.g., repaglinide), sulfonylureas (e.g., glimepiride, glyburide, gliclazide, chlorpropamide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, glycogen phosphorylase inhibitors, inhibitors of fatty acid binding protein (aP2), glucagon-like peptide-1 (GLP-1) and other agonists of the GLP-1 receptor, and dipeptidyl peptidase IV (DPP4) inhibitors.

Other suitable thiazolidinediones include, but are not limited to, MCC-555 (disclosed in U.S. Pat. No. 5,594,016, Mitsubishi), faraglitazar (GI-262570, Glaxo-Wellcome), englitazone (CP-68722, Pfizer) or darglitazone (CP-86325, Pfizer; isaglitazone, MIT/Johnson & Johnson), reglitazar (JTT-501, (JPNT/Pharmacia & Upjohn), rivoglitazone (R-119702, Sankyo/WL), liraglutide (NN-2344, Dr. Reddy/NN), and (Z)-1,4-bis-4-[(3,5-dioxo-1,2,4-oxadiazolidin-2-yl-methyl)]phenoxybut-2-ene (YM-440, Yamanouchi).

Examples of PPAR-alpha agonists, PPAR-gamma agonists and PPAR alpha/gamma dual agonists include, but are not limited to, muraglitazar, peliglitazar, tesaglitazar AR-HO39242 (Astra/Zeneca), GW-501516 (Glaxo-Wellcome), KRP297 (Kyorin Merck), as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841-1847 (1998); WO 01/21602 and in U.S. Pat. No. 6,414,002 and U.S. Pat. No. 6,653,314, the disclosures of which are incorporated herein by reference in their entireties, employing dosages as set out therein. In one embodiment, the compounds designated as preferred in the cited references are preferred for use herein.

Suitable aP2 inhibitors include, but are not limited to, those disclosed in U.S. application Ser. No. 09/391,053, filed Sep. 7, 1999, and in U.S. Pat. No. 6,548,529, the disclosures of which are incorporated herein by reference in their entireties, employing dosages as set out therein.

Suitable DPP4 inhibitors include, but are not limited to, those disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano- (S)-pyrrolidine) (Novartis) as disclosed by Hughes et al, Biochemistry, 38(36), 11597-11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537-1540), 2-cyanopyrrolidides and 4-cyanopyrrolidides, as disclosed by Ashworth et al, Bioorg. & Med. Chem. Lett., Vol. 6, No. 22, pp 1163-1166 and 2745-2748 (1996), the compounds disclosed in U.S. application Ser. No. 10/899,641, WO 01/68603 and U.S. Pat. No. 6,395,767, all of which are incorporated herein by reference in their entireties, employing dosages as set out in the above references. In one embodiment, the DPP4 inhibitor is saxagliptin.

Other suitable meglitinides include nateglinide (Novartis) or KAD1229 (PF/Kissei).

Examples of suitable anti-hyperglycemic agents for use in combination with the formulations of the present invention include, but are not limited to, glucagon-like peptide-1 (GLP-1) such as GLP-1 (1-36) amide, GLP-1 (7-36) amide, GLP-1 (7-37) (as disclosed in U.S. Pat. No. 5,614,492, incorporated herein by reference in its entirety), as well as exenatide (Amylin/Lilly), LY-315902 (Lilly), MK-0431 (Merck), liraglutide (NovoNordisk), ZP-10 (Zealand Pharmaceuticals A/S), CJC-1131 (Conjuchem Inc), and the compounds disclosed in WO 03/033671, incorporated herein by reference in its entirety.

Examples of suitable hypolipidemic/lipid lowering agents for use in combination with the formulations of the present invention include one or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid co-transporter inhibitors, up-regulators of LDL receptor activity, bile acid sequestrants, cholesterol ester transfer protein (e.g., CETP inhibitors, such as torcetrapib (CP-529414, Pfizer) and JTT-705 (Akros Pharma)), PPAR agonists (as described above) and/or nicotinic acid and derivatives thereof. The hypolipidemic agent can be an up-regulator of LD2 receptor activity, such as 1(3H)-isobenzofuranone,3-(β-hydroxy-10-oxotetradecyl)-5,7-dimethoxy-(MD-700, Taisho Pharmaceutical Co. Ltd) and cholestan-3-ol,4-(2-propenyl)-(3a,4a,5a)-(LY295427, Eli Lilly). Preferred hypolipidemic agents include pravastatin, lovastatin, simvastatin, atorvastatin, fluvastatin, cerivastatin, atavastatin and rosuvastatin (ZD-4522), for example.

Examples of MTP inhibitors that can be employed as described above include, but are not limited to, those disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. Pat. No. 5,962,440, all of which are incorporated herein by reference in their entireties.

Examples of HMG CoA reductase inhibitors that can be employed in combination with the formulations of the invention include, but are not limited to, mevastatin and related compounds, as disclosed in U.S. Pat. No. 3,983,140, lovastatin (mevinolin) and related compounds, as disclosed in U.S. Pat. No. 4,231,938, pravastatin and related compounds, such as disclosed in U.S. Pat. No. 4,346,227, simvastatin and related compounds, as disclosed in U.S. Pat. Nos. 4,448,784 and 4,450,171. Other suitable HMG CoA reductase inhibitors that can be employed herein include, but are not limited to, fluvastatin, disclosed in U.S. Pat. No. 5,354,772, cerivastatin, as disclosed in U.S. Pat. Nos. 5,006,530 and 5,177,080, atorvastatin, as disclosed in U.S. Pat. Nos. 4,681,893, 5,273,995, 5,385,929 and 5,686,104, atavastatin (Nissan/Sankyo's nisvastatin (NK-104)), as disclosed in U.S. Pat. No. 5,011,930, rosuvastatin (Shionogi-Astra/Zeneca (ZD-4522)), as disclosed in U.S. Pat. No. 5,260,440, and related statin compounds disclosed in U.S. Pat. No. 5,753,675, pyrazole analogs of mevalonolactone derivatives, as disclosed in U.S. Pat. No. 4,613,610, indene analogs of mevalonolactone derivatives, as disclosed in PCT application WO 86/03488, 6-[2-(substituted-pyrrol-1-yl)-alkyl)pyran-2-ones and derivatives thereof, as disclosed in U.S. Pat. No. 4,647,576, Searle's SC-45355 (a 3-substituted pentanedioic acid derivative) dichloroacetate, imidazole analogs of mevalonolactone, as disclosed in PCT application WO 86/07054, 3-carboxy-2-hydroxy-propane-phosphonic acid derivatives, as disclosed in French Patent No. 2,596,393, 2,3-disubstituted pyrrole, furan and thiophene derivatives, as disclosed in European Patent Application No. 0221025, naphthyl analogs of mevalonolactone, as disclosed in U.S. Pat. No. 4,686,237, octahydronaphthalenes, such as disclosed in U.S. Pat. No. 4,499,289, keto analogs of mevinolin (lovastatin), as disclosed in European Patent Application No. 0142146 A2, and quinoline and pyridine derivatives, as disclosed in U.S. Pat. Nos. 5,506,219 and 5,691,322. All of the cited references are incorporated herein by reference in their entireties. In addition, phosphinic acid compounds useful in inhibiting HMG CoA reductase, such as those disclosed in GB 2205837, are suitable for use in combination with the formulations of the present invention.

Examples of squalene synthetase inhibitors suitable for use herein include, but are not limited to, α-phosphono-sulfonates disclosed in U.S. Pat. No. 5,712,396, those disclosed by Biller et al., J. Med. Chem., 1988, Vol. 31, No. 10, pp. 1869-1871, including isoprenoid (phosphinyl-methyl)phosphonates, as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996). Other squalene synthetase inhibitors suitable for use herein include the terpenoid pyrophosphates disclosed by P. Ortiz de Montellano et al, J. Med. Chem., 1977, 20, 243-249; the farnesyl diphosphate analog A and presqualene pyrophosphate (PSQ-PP) analogs as disclosed by Corey and Volante, J. Am. Chem. Soc., 1976, 98, 1291-1293; phosphinylphosphonates reported by McClard, R. W. et al, J.A.C.S., 1987, 109, 5544; and cyclopropanes reported by Capson, T. L., PhD dissertation, June, 1987, Dept. Med. Chem. U of Utah, Abstract, Table of Contents, pp 16, 17, 40-43, 48-51, Summary. All of the cited references are incorporated herein by reference in their entireties.

Examples of fibric acid derivatives that can be employed in combination the formulations of the invention include, but are not limited to, fenofibrate, gemfibrozil, clofibrate, bezafibrate, ciprofibrate, clinofibrate and the like, probucol, and related compounds, as disclosed in U.S. Pat. No. 3,674,836, bile acid sequestrants, such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly(diallylmethylamine) derivatives, such as disclosed in U.S. Pat. No. 4,759,923, quaternary amine poly(diallyldimethylammonium chloride) and ionenes, such as disclosed in U.S. Pat. No. 4,027,009, and other known serum cholesterol lowering agents. In one embodiment, the fibric acid derivative is probucol or gemfibrozil. All of the cited references are incorporated herein by reference in their entireties.

Examples of ACAT inhibitors that can be employed in combination with the formulations of the invention include, but are not limited to, those disclosed in Drugs of the Future 24, 9-15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77-85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16-30; "RP 73163: a bioavailable alkylsulfinyl-diphenylimidazole ACAT inhibitor", Smith, C., et al, Bioorg. Med. Chem. Lett. (1996), 6(1), 47-50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173-98, Publisher: CRC, Boca Raton, Fla.; "ACAT inhibitors: potential anti-atherosclerotic agents", Sliskovic et al, Curr. Med. Chem. (1994), 1(3), 204-25; "Inhibitors of acyl-CoA:cholesterol O-acyl transferase (ACAT) as hypocholesterolemic agents. The first water-soluble ACAT inhibitor with lipid-regulating activity. Inhibitors of acyl-CoA:cholesterol acyltransferase (ACAT). Development of a series of substituted N-phenyl-N'-[(1-phenylcyclopentyl)methyl]ureas with enhanced hypocholesterolemic activity", Stout et al, Chemtracts: Org. Chem. (1995), 8(6), 359-62, or TS-962 (Taisho Pharmaceutical Co. Ltd). All of the cited references are incorporated herein by reference in their entireties.

Examples of suitable cholesterol absorption inhibitors for use in combination with the formulations of the invention include, but are not limited to, SCH48461 (Schering-Plough), as well as those disclosed in Atherosclerosis 115, 45-63 (1995) and J. Med. Chem. 41, 973 (1998), incorporated herein by reference in its entirety.

Examples of suitable ileal $Na^+$/bile acid co-transporter inhibitors for use in combination with the formulations of the invention include, but are not limited to, compounds as disclosed in Drugs of the Future, 24, 425-430 (1999), incorporated herein by reference in its entirety.

Examples of lipoxygenase inhibitors that can be employed in combination with the formulations of the invention include, but are not limited to, 15-lipoxygenase (15-LO) inhibitors, such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199-1206, and Cornicelli et al., "15-Lipoxygenase and its Inhibition: A Novel Therapeutic Target for Vascular Disease", Current Pharmaceutical Design, 1999, 5, 11-20. All of the cited references are incorporated herein by reference in their entireties.

Examples of suitable anti-hypertensive agents for use in combination with the formulations of the present invention include, but are not limited to, beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates. All of the cited references are incorporated herein by reference in their entireties.

Examples of suitable anti-obesity agents for use in combination with the formulations of the present invention include, but are not limited to, beta 3 adrenergic agonists, lipase inhibitors, serotonin (and dopamine) reuptake inhibitors, thyroid receptor beta drugs, 5HT2C agonists, (such as Arena APD-356); MCHR1 antagonists, such as Synaptic SNAP-7941 and Takeda T-226926, melanocortin receptor (MC4R) agonists, melanin-concentrating hormone receptor (MCHR) antagonists (such as Synaptic SNAP-7941 and Takeda T-226926), galanin receptor modulators, orexin antagonists, CCK agonists, NPY1 or NPY5 antagonist, NPY2 and NPY4 modulators, corticotropin releasing factor agonists, histamine receptor-3 (H3) modulators, 11-beta-HSD-1 inhibitors, adinopectin receptor modulators, monoamine reuptake inhibitors or releasing agents, ciliary neurotrophic factors (CNTF, such as AXOKINE® by Regeneron), BDNF (brain-derived neurotrophic factor), leptin and leptin receptor modulators, cannabinoid-1 receptor antagonists (such as SR-141716 (Sanofi) or SLV-319 (Solvay)), and anorectic agents.

Beta 3 adrenergic agonists that can be optionally employed in combination with formulations of the present invention include, but are not limited to, AJ9677 (Takeda/Dainippon), L750355 (Merck), CP331648 (Pfizer,) or other known beta 3 agonists, as disclosed in U.S. Pat. Nos. 5,541,204, 5,770,615, 5,491,134, 5,776,983 and 5,488,064, all of which are incorporated herein by reference in their entireties.

Examples of lipase inhibitors that can be employed in combination with formulations of the present invention include, but are not limited to, orlistat and ATL-962 (Alizyme).

Serotonin (and dopamine) reuptake inhibitors (or serotonin receptor agonists) that can be employed in combination with the formulations of the present invention include, but are not limited to, BVT-933 (Biovitrum), sibutramine, topiramate (Johnson & Johnson) and axokine (Regeneron).

Examples of thyroid receptor beta compounds that can be employed in combination with formulations of the present invention include, but are not limited to, thyroid receptor ligands, such as those disclosed in WO 97/21993 (U. Cal SF), WO 99/00353 (KaroBio) and WO 00/039077 (KaroBio), incorporated herein by reference it their entireties.

Examples of monoamine reuptake inhibitors that can be employed in combination with the formulations of the present invention include, but are not limited to, fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine and mazindol.

Anorectic agents that can be employed in combination with the formulations of the present invention include, but are not limited to, topiramate (Johnson & Johnson), dexamphetamine, phentermine, phenylpropanolamine and mazindol.

The aforementioned patents and patent applications are incorporated herein by reference.

Where any of the formulations of the invention are used in combination with other therapeutic agent(s), the other therapeutic agent(s) can be used, for example, in the amounts indicated in the Physician's Desk Reference, as in the cited patents and patent applications set out above, or as otherwise known and used by one of ordinary skill in the art.

Where any of the formulations of the invention are used in combination with other therapeutic agent(s), each of the compounds of the combination can be administered simultaneously or sequentially and in any order, and the components can be administered separately or as a fixed combination, in jointly therapeutically effective amounts, for example, in daily dosages as described herein. In one embodiment of the invention, a fixed combination of the invention can be prepared by mixing a dry granulation of the dapagliflozin or dapagliflozin propylene glycol hydrate formulation of the invention and a dry granulation of the other therapeutic agent(s) and filling the mixture into capsules of desired size, shape, color, or other characteristics, or compressed to form tablets.

While this invention has been particularly shown and described with references to preferred embodiments thereof, it will be understood by those skilled in the art that various changes in form and details may be made therein without departing from the scope of the invention encompassed by the appended claims. It will also be clear that the invention may be practiced otherwise than as particularly described in the foregoing description and examples. Numerous modifications and variations of the present invention are possible in light of the above teachings and, therefore, are within the scope of the appended claims.

The following examples are provided to describe the invention in further detail. These examples, which set forth the best mode presently contemplated for carrying out the invention, are intended to illustrate and not to limit the invention.

EXAMPLES

The following working Examples are illustrative of the present invention. All temperatures are expressed in degrees Centigrade unless otherwise indicated.

Example 1

Preparation of Dapagliflozin (Compound I)

The preparation of compounds of structure I is generally described in U.S. Pat. No. 6,414,126, and specifically described in Scheme 1 and Example 1 of U.S. Pat. No. 5,515,117, both of which are incorporated by reference herein in their entireties. Stable forms of compounds of structure (I) can be crystallized as solvates (e.g., hydrates) or complexes.

Example 2A

Preparation of Dapagliflozin (S)-propylene Glycol Hydrate (Ia)

The preparation of structure Ia is described and depicted schematically below.

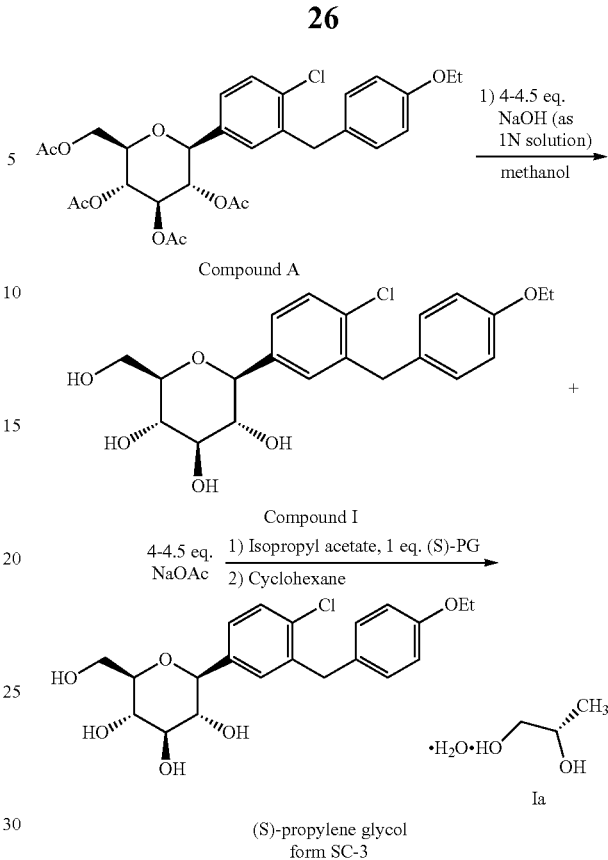

Compound A can be prepared as described in Example 1, Part E of U.S. Pat. No. 6,515,117.

A 10-L glass reactor equipped with a thermocouple and a nitrogen inlet was charged with MeOH (1.25 L), deionized water (3.6 L) followed by 50% aqueous NaOH (205.9 ml, 3.899 mol). The residual solution of NaOH in the measuring cylinder was transferred with water (94 ml) to the reaction vessel. Compound A (503.11 g, 0.872 mol) was added and the mixture was stirred and heated to ~68° C. over 1.5 hour. After 1 hour, the circulation bath temperature was lowered from 80° C. to 70° C.; internal temperature became 65° C. After a total of 3 hours, HPLC indicated completion of reaction, Compound I AP ~99.5. (HPLC: Column: YMC ODS-A (C-18) S3, 4.6×50 mm. Solvent A: 0.2% aq. $H_3PO_4$. Solvent B: 90% $CH_3CN$/10% $H_2O$ Start % B=0, final % B=100 Gradient time 8 min; hold time 3 minutes. Integration stop time 11.0 minutes. Flow rate 2.5 ml/minute. UV wave length 220 nm.)

After the mixture was cooled to 25° C., isopropyl acetate (2.5 L) was added. The mixture was stirred for 10 minutes and then the aqueous layer was separated (pH=12.5) and organic layer was washed with water (1 L). During this wash the pH of the biphasic system was adjusted to 6.0 with concentrated HCl (5.0 ml) and then the aqueous layer was separated. Neutralization before phase split was done to prevent contamination of the product with NaOH. The (S)-propylene glycol structure prepared without neutralization was slightly basic [pH 8.3 of a suspension sonicated in water (~20 mg/ml)].

The organic layer was collected in a separate vessel. The reactor was washed with water (2 L), MeOH (2 L) and flushed with nitrogen gas. The wet solution of compound B was recharged into the reactor and (S)-propylene glycol ((S)-PG) (67.03 g, 0.872 mole) was introduced. Optionally, seed crystals of (S)-PG Ia can be added at this stage. Seed crystals can be prepared by dissolving compound I in a solvent such as MTBE and treating the resulting solution with (S)-propylene glycol and proceeding as described above without the use of seeding.

Instantaneous crystallization produced a thick slurry. After stirring for 1 hour, cyclohexane (2.5 L) was added rapidly over 10 minutes and the stirring was continued for 21 hours. The product was filtered through a filter paper (Whatman #5, Buchner funnel 24" diameter). The filtration was rapid and took about 15 minutes. The filter cake was washed with a mixture (1:1) of MTBE/cyclohexane (2×1 L) and dried under suction for 0.5 hour. The solid was transferred to a pyrex tray and dried under vacuum (25 mm Hg) in an oven at 25-30° C. for two days till water analysis by K.F. corresponded to monohydrate (3.6 wt. %). The (S)-PG product Ia was obtained (0.425 kg, yield 97%) as a snow white solid, mp 71° C., HPLC AP 99.7. (HPLC method: Mobile Phase A: 0.05% TFA in $H_2O$. Mobile Phase B: 0.05% TFA in CAN. Column: YMC Hydrosphere 4.6×150 (34 Gradient: 30-90% B over 45 minutes, hold 5 minutes; back to 30% B and re-equilibrate for 10 min. Wavelength: 220 nm. Injection Volume: 10 μl. Temperature: Ambient).

The (R) form of dapagliflozin can be prepared using these methods and substituting (S)-propylene glycol with (R)-propylene glycol.

Example 2B

Preparation of Dapagliflozin (S)-propylene Glycol Hydrate (compound Ia)

The structure Ia can alternatively be prepared as described and depicted schematically below.

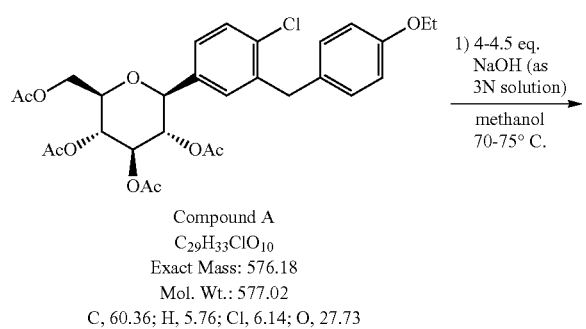

Compound A
$C_{29}H_{33}ClO_{10}$
Exact Mass: 576.18
Mol. Wt.: 577.02
C, 60.36; H, 5.76; Cl, 6.14; O, 27.73

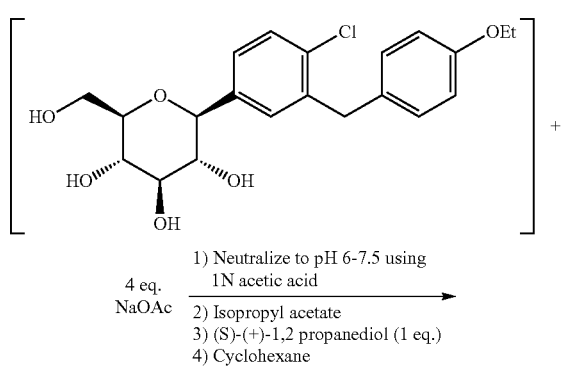

4 eq. NaOAc
1) Neutralize to pH 6-7.5 using 1N acetic acid
2) Isopropyl acetate
3) (S)-(+)-1,2 propanediol (1 eq.)
4) Cyclohexane -continued

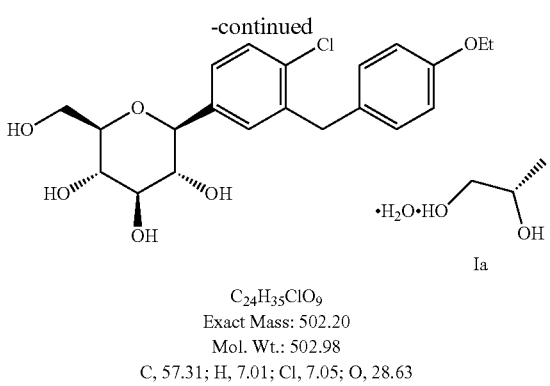

$C_{24}H_{35}ClO_9$
Exact Mass: 502.20
Mol. Wt.: 502.98
C, 57.31; H, 7.01; Cl, 7.05; O, 28.63

20 g of compound A was charged to a reactor at ambient temperature and pressure. 30 mL Methanol and 49.75 mL 3N NaOH were added to the reactor and the reaction mixture was heated to 80° C. or reflux, and held about 2-3 hours for reaction completion <0.5 AP. The batch was cooled to 20° C. and neutralized to pH 6.0-7.5 using 1N acetic acid (requires ~1 mL/gm input).

Extraction: The product was extracted from the reaction mixture into 100 mL isopropyl acetate, the aqueous phase was split away and the organic phase washed with water until conductivity<10 mS (~4 mL/gm input). The aqueous phase was split away.

Crystallization: 2.8 g (1.05 eq) (S)-(+)-1,2 Propanediol 96%+ was added to the reaction mixture. The batch was seeded with 0.1 g compound I seed. 160 mL Cyclohexane was added and the batch cooled to 5° C. The batch was allowed to stir at 5° C. at least 1 hour before isolation.

Isolation and Drying: Each load of isolated cake was washed with 50/50 by volume isopropyl acetate/cyclohexane mixture. The cake was dried at 30° C. in a vacuum oven under full vacuum. (Cake is dry when KF=3.6%-4.1%).

Yield=84% (uncorrected)
Typical purity=99.81AP
Typical PG content=15.1-15.8% by GC Capsules containing the SGLT2 inhibitor of Formula I (dapagliflozin) or Formula Ia (dapagliflozin (S)—Propylene glycol hydrate) were prepared in strengths of 2.5 mg (Example 3), 10 mg (Example 4) and 100 mg (Example 5) as two-piece, gray opaque size #0 (2.5 mg and 10 mg) and size #00 (for 100 mg) hard gelatin capsules.

Example 3

Preparation of Dapagliflozin/Dapagliflozin Propylene Glycol Hydrate Capsule, 2.5 Mg A 25.0 mg of stock granulation was prepared containing 10% dapagliflozin or dapagliflozin propylene glycol hydrate filled in gray, opaque, size #0 capsule shell.

A. Stock Granulation Composition

| Ingredient | Amount (% w/w) |
| --- | --- |
| Dapagliflozin or Dapagliflozin propylene glycol hydrate (Or equivalent amount of Dapagliflozin propylene glycol hydrate) | 10.0 |
| Pregelatinized Starch | 15.0 |
| Microcrystalline Cellulose | 68.75 |
| Sodium Starch Glycolate | 3.0 |

| Ingredient | Amount (% w/w) |
| --- | --- |
| Silicon Dioxide | 2.0 |
| Magnesium Stearate | 1.25 |

The amount of dapagliflozin is theoretically equivalent to 81.29% of dapagliflozin propylene glycol hydrate, either of which can be used. The actual amount of dapagliflozin propylene glycol hydrate will depend on the purity. The microcrystalline cellulose is the compensating excipient whose amount can vary depending on the actual amount of dapagliflozin propylene glycol hydrate and magnesium stearate used. The preferred amount of magnesium stearate is 1.25% (w/w). A useful range is 1.25-1.50% (w/w).

The stock granulation of Part A and the Example 3 capsules were prepared according to the following procedures.

B. Example 3 Stock Granulation Procedure

1. Screen dapagliflozin or dapagliflozin propylene glycol hydrate.
2. Screen silicon dioxide.
3. Mix silicon dioxide with dapagliflozin or dapagliflozin propylene glycol hydrate in a suitable blender.
4. Screen pregelatinized starch and microcrystalline cellulose, if necessary.
5. Add ingredients from Step 4 to a suitable blender.
6. Add mixture from Step 3 to the blend from Step 5, and mix.
7. Screen sodium starch glycolate.
8. Add ingredient from Step 7 to the blend from Step 6, and mix.
9. Screen the blend from Step 8, and mix.
10. Screen portion of magnesium stearate.
11. Add ingredient from Step 10 to the blend from Step 9, and mix.
12. Densify the blend from Step 11.
13. Reduce the densified blend Step 12.
14. Screen the remaining portion of magnesium stearate.
15. Add ingredient from Step 14 to the granulation from Step 13, and mix.

C. Example 3 Product: Dapagliflozin/Dapagliflozin Propylene Glycol Hydrate Capsule, 2.5 mg 1. Fill empty capsule shells with sufficient Example 3 Part A stock granulation for capsules (10.0%) w/w (as the non-solvated form), to provide 2.5 mg capsules.
2. De-dust the capsules.

Example 4

Preparation of Dapagliflozin/Dapagliflozin Propylene Glycol Hydrate Capsule, 10 mg A. Stock Granulation Composition Stock granulation composition was prepared as described in Example 3A.

B. Example 4 Stock Granulation Procedure

Stock granulation procedure was performed as described in Example 3B.

C. Example 4 Product: Dapagliflozin Capsule, 10 mg

1. Fill empty capsule shells with Example 3 Part A stock granulation for capsules (10.0% w/w as the non-solvated form), to provide 10 mg capsules.
2. De-dust the capsules.
3. Weight sort the capsules.

Example 5

Preparation of Dapagliflozin/Dapagliflozin Propylene Glycol Hydrate Capsule, 100 mg Composition: 438.6 mg of dapagliflozin (Example 5 Part A) Stock Granulation for Capsules (22.8% w/w), filled in Gray, Opaque, Size #0 Capsule Shell was prepared.

A. Stock Granulation Composition

| Ingredient | Amount (% w/w) |
| --- | --- |
| Dapagliflozin or Dapagliflozin propylene glycol hydrate (Or equivalent amount of Dapagliflozin propylene glycol hydrate) | 22.8 |
| Pregelatinized Starch | 15.0 |
| Microcrystalline Cellulose | 55.95 |
| Sodium Starch Glycolate | 3.0 |
| Silicon Dioxide | 2.0 |
| Magnesium Stearate | 1.25 |

The amount of dapagliflozin is theoretically equivalent to 81.29% of dapagliflozin propylene glycol hydrate, either of which can be used. The actual amount of dapagliflozin propylene glycol hydrate will depend on the purity. The microcrystalline cellulose is the compensating excipient whose amount can vary depending on the actual amount of dapagliflozin propylene glycol hydrate and magnesium stearate used. The preferred amount of magnesium stearate is 1.25% (w/w). A useful range is 1.25-1.50% (w/w).

The stock granulation of Part 5A and the Example 5 capsules were prepared according to the following procedures.

B. Stock Granulation Procedure

1. Screen silicon dioxide.
2. Mix silicon dioxide with dapagliflozin or dapagliflozin propylene glycol hydrate in a suitable blender.
3. Screen the blend from Step 2, and mix again.
4. Screen pregelatinized starch and microcrystalline cellulose, if necessary.
5. Add ingredients form Step 4 to the blend from Step 3, and mix.
6. Screen sodium starch glycolate.
7. Add ingredient from Step 6 to the blend from Step 5, and mix.
8. Screen a portion of magnesium stearate.
9. Add ingredient from Step 8 to the blend from Step 7, and mix.
10. Densify the blend from Step 9.
11. Reduce the densified blend from Step 10.
12. Screen the remaining portion of magnesium stearate.
13. Add ingredient from Step 12 to the granulation from Step 11, and mix.

C. Example 5 Product: Dapagliflozin/Dapagliflozin Propylene Glycol Hydrate Capsule, 100 mg 1. Fill empty capsule shells with Example 5 stock granulation for capsules (22.8% w/w as the non-solvated form).
2. De-dust the capsules.
3. Weight sort the capsules.

The formed capsules of Example 3 (2.5 mg), Example 4 (10 mg), and Example 5 (100 mg) are used in treating metabolic disorders, including obesity.

Example 6

Treatment of Metabolic Disorders

An oral solution (0.5 mg/mL) was prepared by dissolving dapagliflozin or dapagliflozin propylene glycol hydrate in a mixture of polyethylene glycol 400, NF and water (USP or purified water) 30:70% v/v. The oral solution was clear and colorless.

The glucosuric effects of dapagliflozin propylene glycol hydrate results in significant loss of calories in the urine versus a known SGLT2 inhibitor (GSK 869,682). The results of an indirect comparison of two single ascending dose studies of SGLT2 inhibitors is described. The amount of glucose excretion/day in healthy subjects taking 50, 100, 200 or 500 mg of GSK 869,682 was approximately 5 g, 6 g, 12 g, and 16 g, respectively. The amount of glucose excretion/day in healthy subjects taking 5, 20, 50 or 100 mg of dapagliflozin propylene glycol hydrate was approximately 30 g, 55 g, 60 g, and 70 g, respectively. The results of the dapagliflozin propylene glycol hydrate study was further confirmed in a 14-day multiple ascending dose phase 2a study in subjects with type 2 diabetes. Patients with type 2 diabetes were treated with placebo, 5 mg dapagliflozin propylene glycol hydrate, 25 mg dapagliflozin propylene glycol hydrate, or 100 mg dapagliflozin propylene glycol hydrate. Results from the 24-hour glucose excretion show that subjects taking 5 mg, 25 mg, and 100 mg dapagliflozin propylene glycol hydrate had significantly higher urine glucose excretion compared to subjects taking placebo.

Diet-Induced Obesity in Rats

Obesity was induced in male Sprague-Dawley rats (mean baseline weight=220 g) via ad libitum access to 2 diets: normal diet (Harlan Teklad rat chow; 3.5 kcal/gm, 5% vegetable fat) and high-sucrose/high-fat diet (Research Diets D12327; 4.6 kcal/gm, 40% sucrose and 40% vegetable fat). Rats under these conditions typically consume approximately 30 g/day of the high-sucrose/high-fat chow and 2 g/day of the normal Harlan Teklad rat chow. A 220-g rat given access to both diets will weigh approximately 750 g after 10 weeks.

Acute Glucosuria Study

Dapagliflozin propylene glycol hydrate (1, 5, or 10 mg/kg) or placebo (vehicle) was orally administered to diet-induced obese (DIO) rats after 24-hour baseline urine samples were collected. Urine volume and glucose concentration were used to determine total urine glucose loss over 24 hours post dose.

Total urine glucose was determined after 24 hours administration of dapagliflozin propylene glycol hydrate. Total glucose lost was calculated as volume of urine x glucose concentration. The results showed that the total amount of glucose lost over 24 hours post dose was significantly increased with increasing doses of dapagliflozin propylene glycol hydrate in a dose-dependent manner.

Chronic Weight Loss Study

DIO rats were sorted into treatment groups based on body weight, total kilocalories consumed, and body composition (via echo MRI). Dapagliflozin propylene glycol hydrate (0.5, 1, or 5 mpk) or placebo was orally administered to DIO rats for 28 days. To assess the importance of compensatory overeating in drug-treated animals, a subgroup of rats that received 5 mg/kg of dapagliflozin propylene glycol hydrate was restricted to the food intake of the placebo group. Body weight and the weight of both diets were determined daily. Respiratory quotient data were obtained on days 2 and 15 of the study, echo MRI was obtained on day 22, and blood was collected for a fasting clinical chemistry tests on day 27.

Chronically administered dapagliflozin propylene glycol hydrate (administered daily over 25 days) produced significant weight loss ($p<0.05$ versus vehicle) in diet-induced obese rats. If the compound-induced overeating was prevented (dapagliflozin propylene glycol hydrate mg/kg pair fed to vehicle group), then the weight loss was greater. Percent weight changes were calculated as daily weight—day 0 weight×100.

Weight Loss in Patients with Type II Diabetes

Treatment naive type II diabetes mellitus patients, n=389, with inadequate blood glycemic control and low mean glucosuria at baseline were given once-daily oral treatments with dapagliflozin propylene glycol hydrate (2.5, 5, 10, 20, or 50 mgs), metformin XR® (750 mg titrated to 1500 mgs), or placebo over 12-weeks.

Treatment with dapagliflozin propylene glycol hydrate resulted in consistent and sustained increases in urinary glucose excretion, rising to mean glucosuria values between 51.8 g/day to 85.0 g/day at week 12 from baseline means between 5.8 grams/day to 10.9 grams/day. Mean glucosuria with placebo and metformin both remained low, 5.7 grams/day and 5.6 grams/day respectively at week 12. A higher proportion of patients in each of the dapagliflozin propylene glycol hydrate groups achieved a 5% weight reduction over those patients taking placebo. Mean percent reductions for body weight and absolute changes in body mass index (BMI) over 12 weeks are shown in Table III.

TABLE III

|  | Dapagliflozin-PGS Dose | | | | | | |
| --- | --- | --- | --- | --- | --- | --- | --- |
|  | 2.5 mgs n = 59 | 5 mgs n = 58 | 10 mgs n = 47 | 20 mgs n = 59 | 50 mgs n = 56 | Placebo n = 54 | Metformin n = 56 |
| Baseline weight (kg) | 90 | 89 | 86 | 88 | 91 | 89 | 88 |
| Mean reduction in weight (%) | −2.7 | −2.5 | −2.7 | −3.4 | −3.4 | −1.2 | −1.7 |
| Baseline BMI (kg/m$^2$) | 31 | 31 | 30 | 31 | 32 | 32 | 32 |
| Mean reduction in BMI | −0.9 | −0.8 | −0.8 | −1.0 | −1.1 | −0.3 | −0.5 |

Example 7

Preparation of Dapagliflozin/Dapagliflozin Propylene Glycol Hydrate Tablet, 2.5 mg Tablets containing the SGLT2 inhibitor dapagliflozin or dapagliflozin propylene glycol hydrate were prepared in strengths of 2.5 mg (Example 7), 10 mg (Example 8) and 50 mg (Example 9) as described below.

Product: Dapagliflozin/Dapagliflozin Propylene Glycol Hydrate Tablet, 2.5 Mg

A. Tablet Composition

| Ingredient | Amount |
| --- | --- |
| Dapagliflozin propylene glycol hydrate (Or equivalent amount of Dapagliflozin) | 3.08 mg |
| Microcrystalline Cellulose | 67.11 mg |
| Anhydrous Lactose | 25.00 mg |
| Crospovidone | 8.75 mg |
| Croscarmellose Sodium | 3.75 mg |
| Talc | 12.50 mg |
| Silicon Dioxide | 2.88 mg |
| Magnesium Stearate | 1.94 mg |

The amount of dapagliflozin is theoretically equivalent to 81.29% of dapagliflozin propylene glycol hydrate, either of which can be used. The actual amount of dapagliflozin propylene glycol hydrate will depend on the purity. The microcrystalline cellulose is the compensating excipient whose amount can vary depending on the actual amount of dapagliflozin propylene glycol hydrate and magnesium stearate used. The target amount of magnesium stearate is 1.94 mg. An acceptable range is about 1.55 to about 2.33 mg.

The stock granulation of Part 7A and the Example 7 tablets were prepared according to the following procedures.

B. Stock Granulation Procedure

1. Deaggregate dapagliflozin propylene glycol hydrate or dapagliflozin and magnesium stearate separately using a suitable screen.

2. Mix dapagliflozin propylene glycol hydrate or dapagliflozin with a portion of microcrystalline cellulose in a suitable mixer; pass through a mill; and transfer it into a suitable blender.

3. "Dry Rinse" the mixer used for mixing Step 2 with a portion of microcrystalline cellulose.

4. Add the blend from Step 3 to the blend from Step 2.

5. Mix the mixture from Step 4 with remaining microcrystalline cellulose, portion of crospovidone, portion of croscarmellose sodium, portion of silicon dioxide and Anhydrous Lactose.

6. Add talc and intragranular magnesium stearate to the mixture from Step 5 and mix.

7. Compact the powder blend from Step 6.

8. Reduce compact from Step 7 to form granules.

9. Mix the granules from Step 8 with remaining amounts of crospovidone, croscarmellose sodium and silicon dioxide.

10. Mix the granules from Step 9 with remaining amount of magnesium stearate.

C. Example 7 Product: Dapagliflozin/Dapagliflozin Propylene Glycol Hydrate Tablet, 2.5 mg 1. Setup the tabletting equipment.

2. Compress the Example 7 stock granulation into tablets.

Example 8

Preparation of Dapagliflozin/Dapagliflozin Propylene Glycol Hydrate Tablet, 10 mg Product: Dapagliflozin/Dapagliflozin Propylene Glycol Hydrate Tablet, 10 Mg A. Tablet Composition

| Ingredient | Amount |
| --- | --- |
| Dapagliflozin propylene glycol hydrate (Or equivalent amount of Dapagliflozin) | 12.30 mg |
| Microcrystalline Cellulose | 57.89 mg |
| Anhydrous Lactose | 25.00 mg |
| Crospovidone | 8.75 mg |
| Croscarmellose Sodium | 3.75 mg |
| Talc | 12.50 mg |
| Silicon Dioxide | 2.88 mg |
| Magnesium Stearate | 1.94 mg |

The amount of dapagliflozin is theoretically equivalent to 81.29% of dapagliflozin propylene glycol hydrate, either of which can be used. The actual amount of dapagliflozin propylene glycol hydrate will depend on the purity. The microcrystalline cellulose is the compensating excipient whose amount can vary depending on the actual amount of dapagliflozin propylene glycol hydrate and magnesium stearate used. The target amount of magnesium stearate is 1.94 mg. An acceptable range is about 1.55 to about 2.33 mg.

The stock granulation of Part 8A and the Example 8 tablets were prepared according to the following procedures.

B. Stock Granulation Procedure

1. Deaggregate dapagliflozin propylene glycol hydrate or dapagliflozin and magnesium stearate separately using a suitable screen.

2. Mix microcrystalline cellulose, dapagliflozin propylene glycol hydrate or dapagliflozin, portion of crospovidone, portion of croscarmellose sodium, portion of silicon dioxide and anhydrous lactose in a suitable blender.

3. Add talc and intragranular magnesium stearate to the mixture from Step 2 and mix in a suitable blender.

4. Compact the powder blend from Step 3.

5. Reduce compact from Step 4 to form granules.

6. Mix the granules from Step 5 with remaining amounts of crospovidone, croscarmellose sodium and silicon dioxide.

7. Mix the granules from Step 6 with remaining amount of magnesium stearate.

C. Example 8—Product: Dapagliflozin/Dapagliflozin Propylene Glycol Hydrate Tablet, 10 Mg 1. Setup the tabletting equipment.

2. Compress the Example 8 stock granulation into tablets.

Example 9

Preparation of Dapagliflozin/Dapagliflozin Propylene Glycol Hydrate Tablet, 50 mg Product: Dapagliflozin/Dapagliflozin Propylene Glycol Hydrate Tablet, 50 Mg
A. Tablet Composition

| Ingredient | Amount |
|---|---|
| Dapagliflozin propylene glycol hydrate (Or equivalent amount of Dapagliflozin) | 61.66 mg |
| Microcrystalline Cellulose | 114.09 mg |
| Anhydrous Lactose | 62.60 mg |
| Crospovidone | 21.91 mg |
| Croscarmellose Sodium | 9.39 mg |
| Talc | 31.30 mg |
| Silicon Dioxide | 7.20 mg |
| Magnesium Stearate | 4.85 mg |

The amount of dapagliflozin is theoretically equivalent to 81.29% of dapagliflozin propylene glycol hydrate, either of which can be used. The actual amount of dapagliflozin propylene glycol hydrate will depend on the purity. The microcrystalline cellulose is the compensating excipient whose amount can vary depending on the actual amount of dapagliflozin propylene glycol hydrate and magnesium stearate used. The target amount of magnesium stearate is 4.85 mg. An acceptable range is about 3.76 to about 5.95 mg.

The stock granulation of Part 9A and the Example 9 tablets were prepared according to the following procedures.

B. Stock Granulation Procedure

1. Mix dapagliflozin propylene glycol hydrate or dapagliflozin, microcrystalline cellulose, anhydrous lactose, crospovidone, croscarmellose sodium, talc and silicon dioxide in a suitable blender.
2. Pass the mixture from Step 1 through a suitable mill.
3. Determine the yield from Step 1 and calculate the amount of magnesium stearate required.
4. Mix the mixture from Step 2 in a suitable blender.
5. Mix the mixture from Step 4 with magnesium stearate.
6. Dry granulate the powder blend from Step 5.
7. Size the granulation from Step 6.
8. Determine the yield based on Step 7.
9. Mix the granules from Step 8 with remaining amount of crospovidone, croscarmellose sodium and silicon dioxide.
10. Mix the granules from Step 9 with remaining amount of magnesium stearate.

C. Example 9 Product: Dapagliflozin/Dapagliflozin Propylene Glycol Hydrate Tablet, 50 mg 1. Setup the tabletting equipment.
2. Compress the Example 9 stock granulation into tablets.

Example 10

Preparation of Dapagliflozin/Dapagliflozin Propylene Glycol Hydrate Tablets (10-, 25-, and 40 mg)

Product: Dapagliflozin/Dapagliflozin Propylene Glycol Hydrate Tablets (10 Mg, 25 mg, and 40 mg)
A. Granulation Composition (% w/w)

| Ingredient | Formulation % w/w |
|---|---|
| Dapagliflozin propylene glycol hydrate (Or equivalent amount of Dapagliflozin) | 9.84 |
| Microcrystalline Cellulose | 63.91 |
| Anhydrous Lactose | 20 |
| Crospovidone | 4 |
| Silicon Dioxide | 1.5 |
| Magnesium Stearate | 0.75 |

B. Stock Granulation Procedure:

1. Mix dapagliflozin propylene glycol hydrate or dapagliflozin with microcrystalline cellulose.
2. Pass the mixture from step 1 through a suitable mill.
3. Mix the blend from step 2 with microcrystalline cellulose, lactose anhydrous, crospovidone, and silicon dioxide.
4. Mix the blend from step 3 with magnesium stearate.
5. Dry granulate the powder blend from Step 4.
6. Size the granulation from Step 5 using appropriate sieve(s).
7. Determine the yield based on step 6.
8. Mix the granules from Step 7 with remaining amount of crospovidone, and silicon dioxide.
9. Mix granules from step 8 with remaining amount of magnesium stearate.

Tablets or capsules of various strengths (8-50 mg) can be prepared using different weights of this granulation using tabletting procedure described above.

Tabletting/capsule filling operations: Same as other formulations provided herein.

Film coating: Hydroxypropylmethyl cellulose, titanium dioxide, polyethylene glycol, and colorant. Alternative film coating: Polyvinyl alcohol (PVA), titanium dioxide, polyethylene glycol, talc, and colorant.

Example 11

Preparation of Dapagliflozin/Dapagliflozin Propylene Glycol Hydrate Tablets (1, 2.5, 5, 10 mg)

Product: Dapagliflozin/Dapagliflozin Propylene Glycol Hydrate Tablets 1, 2.5, 5, 10 mg
A. Granulation Composition

| Ingredient | 1 mg Tablet | 2.5 mg Tablet | 5 mg Tablet | 10 mg Tablet |
|---|---|---|---|---|
| Dapagliflozin propylene glycol hydrate (Or equivalent amount of Dapagliflozin) | 1.23 mg | 3.075 mg | 6.15 mg | 12.30 mg |
| Microcrystalline Cellulose | 50-90 mg | 60-115 mg | 60-115 mg | 120-230 mg |
| Lactose | 10-30 mg | 12.5-38 mg | 12.5-38 mg | 25-75 mg |
| Crospovidone | 2-10 mg | 2.5-13 mg | 2.5-13 mg | 5-25 mg |
| Silicon Dioxide | 0.5-4 mg | 0.6-5 mg | 0.6-5 mg | 1-10 mg |
| Magnesium Stearate | 0.5-2.0 mg | 0.6-2.5 mg | 0.6-2.5 mg | 1-5 mg |
| Antioxidant and/or chelating agent | 0-0.5 mg | 0-0.6 mg | 0-0.6 mg | 0-1.25 mg |

B. Stock Granulation Procedure

1. Mix dapagliflozin propylene glycol hydrate or dapagliflozin with microcrystalline cellulose.
2. Pass the mixture from step 1 through a suitable mill.
3. Mix the blend from step 2 with microcrystalline cellulose, lactose anhydrous, crospovidone, silicon dioxide.
4. Mix the blend from step 3 with magnesium stearate.
5. Dry granulate the powder blend from Step 4.
6. Size the granulation from Step 5 using appropriate sieve(s).
7. Determine the yield based on step 6.
8. Mix the granules from Step 7 with remaining amount of crospovidone, and silicon dioxide.
9. Mix granules from step 8 with remaining amount of magnesium stearate.

Tablets or capsules of various strengths (1-20 mg) can be prepared using different weights of this granulation.

Tabletting/capsule filling operations: Same as other formulations provided herein.

Film coating: Polyvinyl alcohol (PVA), titanium dioxide, polyethylene glycol, talc, and colorant.

What is claimed is:

1. An immediate release pharmaceutical formulation comprising a dapagliflozin propylene glycol hydrate selected from the (S)-propylene glycol hydrate having the formula

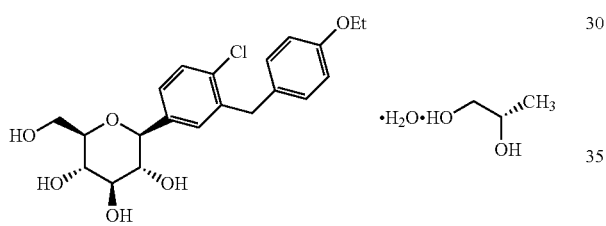

and the (R)-propylene glycol hydrate having the formula

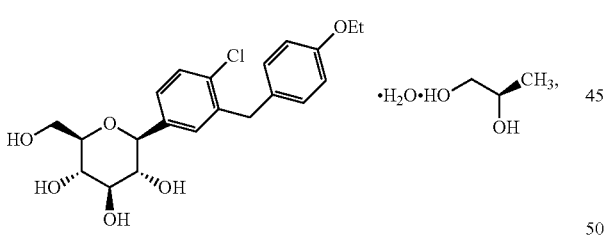

and a pharmaceutically acceptable carrier, in a form selected from the group consisting of a tablet, a stock granulation, and a capsule, wherein the dapagliflozin propylene glycol hydrate is present in an amount to provide a daily dose within the range of from about 0.1 to about 750 mg per day in single or divided doses or multiple doses, which is administered 1 to 4 times, wherein the dapagliflozin propylene glycol hydrate is present in an amount within the range of from 0.1% to 70% of tablet or capsule fill; and the pharmaceutically acceptable carrier comprises:
one or more bulking agents/binders in an amount within the range of from 1% to 95% by weight of tablet or capsule fill, the one or more bulking agents/binders comprising one or more of anhydrous lactose in an amount within the range of 0% to 95% by weight of tablet or capsule fill, microcrystalline cellulose in an amount within the range of 0% to 95% by weight of tablet or capsule fill, and pregelatinized starch in an amount within the range of 0 to 95% by weight of tablet or capsule fill;
one or more disintegrants in an amount within the range of from 0% to 20% by weight of tablet or capsule fill, the one or more disintegrants comprising one or more of croscarmellose sodium in an amount within the range of 0% to 20% by weight of tablet or capsule fill, crospovidone in an amount within the range of 0% to 12% by weight of tablet or capsule fill, and sodium starch glycolate in an amount within the range of 0% to 20% by weight of tablet or capsule fill;
one or more glidants and/or anti-adherents comprising one or more of talc and silicon dioxide in an amount within the range from 0% to 10% by weight of tablet or capsule fill; and
one or more lubricants comprising magnesium stearate in an amount within the range of 0.1% to 5% by weight of tablet or capsule fill.

2. The pharmaceutical formulation according to claim 1, wherein the dapagliflozin propylene glycol hydrate is the (R)-propylene glycol hydrate having the formula

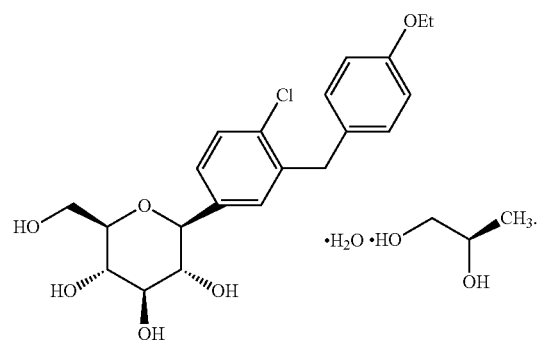

3. The formulation according to claim 1 in the form of a stock granulation for loading in capsules or forming tablets.

4. The formulation according to claim 1, in capsule form.

5. The formulation according to claim 1, in tablet form.

6. The formulation according to claim 1 comprising:
a) dapagliflozin propylene glycol hydrate, wherein the dapagliflozin propylene glycol hydrate is present in an amount within the range of from about 0.1% to about 30% by weight of tablet or capsule fill;
b) bulking agents in a total amount within the range of from about 10% to about 85% by weight of tablet or capsule fill comprising one or more of lactose present in an amount within the range of from about 20% to about 75% by weight of tablet or capsule fill, and microcrystalline cellulose present in an amount within the range of from about 20% to about 75% by weight of tablet or capsule fill;
c) a binder comprising pregelatinized starch present in an amount within the range of from about 10% to about 75% by weight of tablet or capsule fill;
d) disintegrants in a total amount within the range of from about 2% to about 10% by weight of tablet or capsule fill, comprising one or more of croscarmellose sodium present in an amount within the range of from about 2% to about 10% by weight of tablet or capsule fill, crospovidone present in an amount within the range of from about 4% to about 10% by weight of tablet or capsule fill, and sodium starch glycolate present in an amount within the range of from about 2% to about 10% by weight of tablet or capsule fill;

e) one or more glidants and/or anti-adherents comprising talc and/or silicon dioxide, wherein the total amount of glidant and/or anti-adherent is present in an amount within the range of from about 1% to about 10% by weight of tablet or capsule fill;

f) a lubricant comprising magnesium stearate present in an amount within the range of from about 0.2% to about 2% by weight of tablet or capsule fill; and g) optionally further comprising an outer protective coating layer comprising a coating polymer and optionally comprising one or more of the following: a plasticizer(s), anti-tacking agent(s), glidant(s), and colorant(s), wherein the total amount of the outer protective coating layer is present in an amount within the range of from about 1% to about 5% by weight of tablet or capsule fill.

7. The formulation according to claim 6, wherein the dapagliflozin propylene glycol hydrate is the (S)-propylene glycol hydrate having the formula

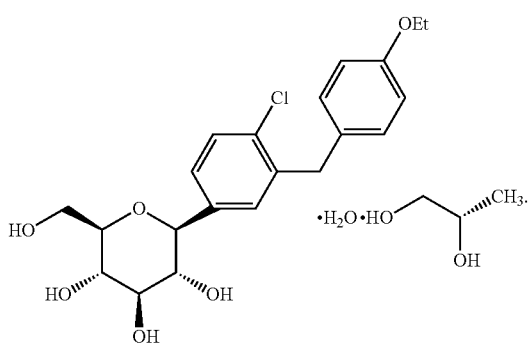

8. The formulation according to claim 1 in the form of a capsule filled with a stock granulation comprising:
   a) dapagliflozin propylene glycol hydrate, wherein the dapagliflozin propylene glycol hydrate is present in an amount of 10% by weight of capsule fill;
   b) microcrystalline cellulose, wherein the microcrystalline cellulose is present in an amount of 68.75% by weight of capsule fill;
   c) pregelatinized starch, wherein the pregelatinized starch is present in an amount of 15% by weight of capsule fill;
   d) sodium starch glycolate, wherein the sodium starch glycolate is present in an amount of 3% by weight of capsule fill;
   e) silicon dioxide, wherein the silicon dioxide is present in an amount of 2% by weight of capsule fill; and
   f) magnesium stearate, wherein the magnesium stearate is present in an amount of 1.25% by weight of capsule fill.

9. The formulation according to claim 8, wherein the dapagliflozin propylene glycol hydrate is the (S)-propylene glycol hydrate having the formula

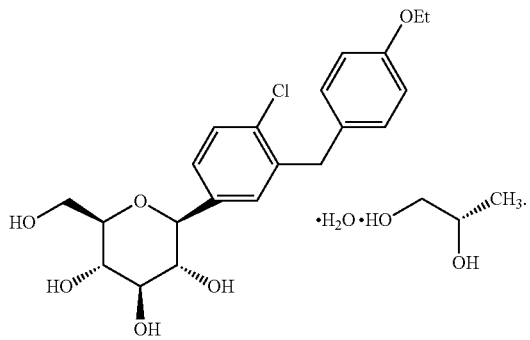

10. The formulation according to claim 1 in the form of a capsule filled with a stock granulation comprising:
    a) dapagliflozin propylene glycol hydrate, wherein the dapagliflozin propylene glycol hydrate is present in an amount of 22.8% by weight of capsule fill;
    b) microcrystalline cellulose, wherein the microcrystalline cellulose is present in an amount of 55.95% by weight of capsule fill;
    c) pregelatinized starch, wherein the pregelatinized starch is present in an amount of 15% by weight of capsule fill;
    d) sodium starch glycolate, wherein the sodium starch glycolate is present in an amount of 3% by weight of capsule fill;
    e) silicon dioxide, wherein the silicon dioxide is present in an amount of 2% by weight of capsule fill; and
    f) magnesium stearate, wherein the magnesium stearate is present in an amount of 1.25% by weight of capsule fill.

11. The formulation according to claim 10, wherein the dapagliflozin propylene glycol hydrate is the (S)-propylene glycol hydrate having the formula

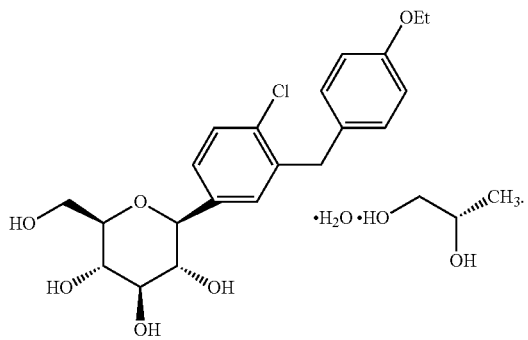

12. The formulation according to claim 1 in the form of a 2.5 mg dapagliflozin dose tablet comprising:
    a) dapagliflozin propylene glycol hydrate, wherein the dapagliflozin propylene glycol hydrate is present in an amount of 3.08 mg;
    b) microcrystalline cellulose, wherein the microcrystalline cellulose is present in an amount of 67.11 mg;
    c) anhydrous lactose, wherein the anhydrous lactose is present in an amount of 25 mg;

d) crospovidone, wherein the crospovidone is present in an amount of 8.75 mg;
e) croscarmellose sodium, wherein the croscarmellose sodium is present in an amount of 3.75 mg;
f) talc, wherein the talc is present in an amount of 12.5 mg;
g) silicon dioxide, wherein the silicon dioxide is present in an amount of 2.88 mg; and
h) magnesium stearate, wherein the magnesium stearate is present in an amount of 1.94 mg.

13. The formulation according to claim 12, wherein the dapagliflozin propylene glycol hydrate is the (S)-propylene glycol hydrate having the formula

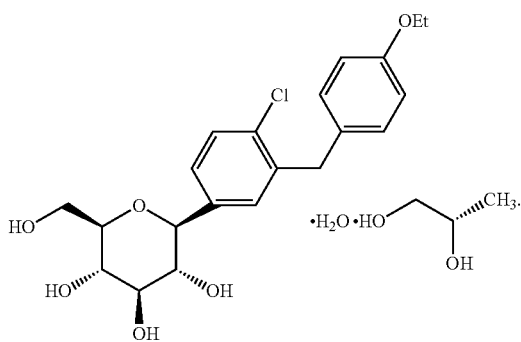

14. The formulation according to claim 1 in the form of a 10 mg dapagliflozin dose tablet comprising:
a) dapagliflozin propylene glycol hydrate, wherein the dapagliflozin propylene glycol hydrate is present in an amount of 12.3 mg;
b) microcrystalline cellulose, wherein the microcrystalline cellulose is present in an amount of 57.89 mg;
c) anhydrous lactose, wherein the anhydrous lactose is present in an amount of 25 mg;
d) crospovidone, wherein the crospovidone is present in an amount of 8.75 mg;
e) croscarmellose sodium, wherein the croscarmellose sodium is present in an amount of 3.75 mg;
f) talc, wherein the talc is present in an amount of 12.5 mg;
g) silicon dioxide, wherein the silicon dioxide is present in an amount of 2.88 mg; and
h) magnesium stearate, wherein the magnesium stearate is present in an amount of 1.94 mg.

15. The formulation according to claim 14, wherein the dapagliflozin propylene glycol hydrate is the (S)-propylene glycol hydrate having the formula

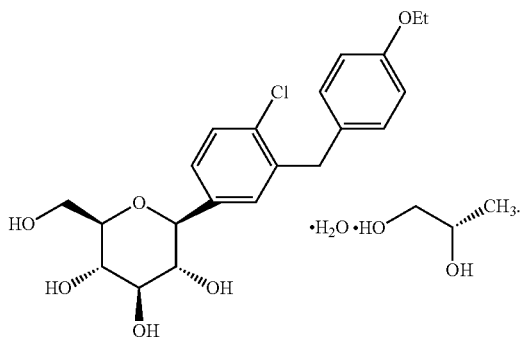

16. The formulation according to claim 1 in the form of a 50 mg dapagliflozin dose tablet comprising:
a) dapagliflozin propylene glycol hydrate, wherein the dapagliflozin propylene glycol hydrate is present in an amount of 61.66 mg;
b) microcrystalline cellulose, wherein the microcrystalline cellulose is present in an amount of 114.09 mg;
c) anhydrous lactose, wherein the anhydrous lactose is present in an amount of 62.6 mg;
d) crospovidone, wherein the crospovidone is present in an amount of 21.91 mg;
e) croscarmellose sodium, wherein the croscarmellose sodium is present in an amount of 9.39 mg;
f) talc, wherein the talc is present in an amount of 31.3 mg;
g) silicon dioxide, wherein the silicon dioxide is present in an amount of 7.2 mg; and
h) magnesium stearate, wherein the magnesium stearate is present in an amount of 4.85 mg.

17. The formulation according to claim 16, wherein the dapagliflozin propylene glycol hydrate is the (S)-propylene glycol hydrate having the formula

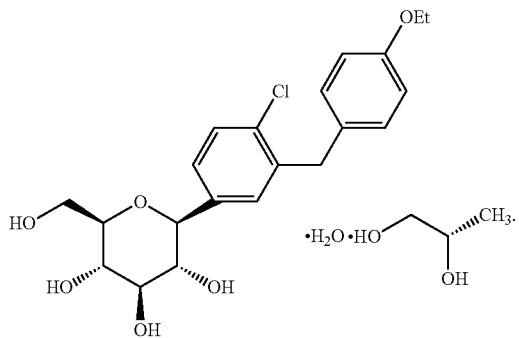

18. The formulation according to claim 1, wherein the dapagliflozin propylene glycol hydrate is present in an amount within the range of from about 0.1% to about 30% of the stock granulation;

the one or more bulking agents are selected from microcrystalline cellulose and anhydrous lactose, present in an amount within the range of from about 10% to about 85% by weight of the stock granulation;

a separate binder is not present;

the disintegrant is selected from crospovidone and croscarmellose sodium present in an amount within the range of from about 0.25% to about 10% by weight of the stock granulation;

the glidant and/or anti-adherent is selected from talc and silicon dioxide present in an amount within the range from about 1% to about 15% by weight of the stock granulation; and the lubricant is magnesium stearate present in an amount within the range from about 0.2% to about 2% by weight of the stock granulation.

19. The formulation according to claim 18, wherein the dapagliflozin propylene glycol hydrate is the (S)-propylene glycol hydrate having the formula

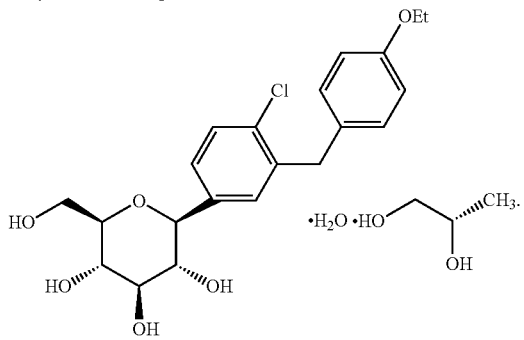

20. The formulation as defined in claim 1 in the form of a tablet or capsule, wherein
the dapagliflozin propylene glycol hydrate is present in an amount within the range of from 0.1% to 30% of tablet or capsule fill; and
the pharmaceutically acceptable carrier comprises:
one or more bulking agents/binders in an amount within the range of from 10 to 85% by weight of tablet or capsule fill, the one or more bulking agents/binders comprising one or more of anhydrous lactose in an amount within the range of 20 to 75% by weight of tablet or capsule fill, microcrystalline cellulose in an amount within the range of 20 to 75% by weight of tablet or capsule fill, and pregelatinized starch in an amount within the range of 10 to 75% by weight of tablet or capsule fill;
one or more disintegrants in an amount within the range of from 0.25 to 10% by weight of tablet or capsule fill, the one or more disintegrants comprising one or more of croscarmellose sodium in an amount within the range of 2 to 10% by weight of tablet or capsule fill, crospovidone in an amount within the range of 4 to 10% by weight of tablet or capsule fill, and sodium starch glycolate in an amount within the range of 2 to 10% by weight of tablet or capsule fill;
one or more glidants and/or anti-adherents comprising one or more of talc and silicon dioxide in an amount within the range from 1 to 4% by weight of tablet or capsule fill; and
one or more lubricants comprising magnesium stearate in an amount within the range of 0.2 to 2% by weight of tablet or capsule fill.

21. The formulation according to claim 20, wherein the dapagliflozin propylene glycol hydrate is the (S)-propylene glycol hydrate having the formula

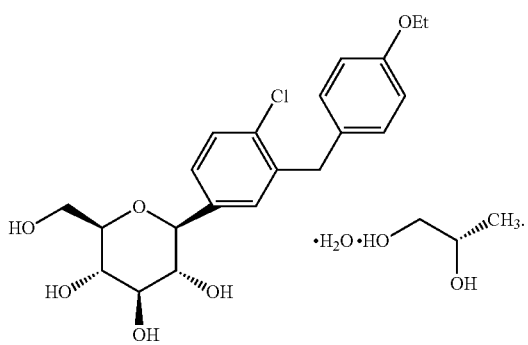

22. The formulation according to claim 20 in the form of a tablet or capsule, wherein
the dapagliflozin propylene glycol hydrate is present in an amount within the range of from 0.1% to 30% of tablet or capsule fill;
the one or more bulking agents/binders are anhydrous lactose in an amount within the range of 20% to 75% by weight of tablet or capsule fill, and microcrystalline cellulose in an amount within the range of 20% to 75% by weight of tablet or capsule fill;
the one or more disintegrants are croscarmellose sodium in an amount within the range of 2% to 10% by weight of tablet or capsule fill, and crospovidone in an amount within the range of 4% to 10% by weight of tablet or capsule fill;
the one or more glidants and/or anti-adherents are talc and silicon dioxide in an amount within the range from 1% to 10% by weight of tablet or capsule fill; and
the one or more lubricants are magnesium stearate in an amount within the range of 0.2% to 2% by weight of tablet or capsule fill.

23. The formulation according to claim 22, wherein the dapagliflozin propylene glycol hydrate is the (S)-propylene glycol hydrate having the formula

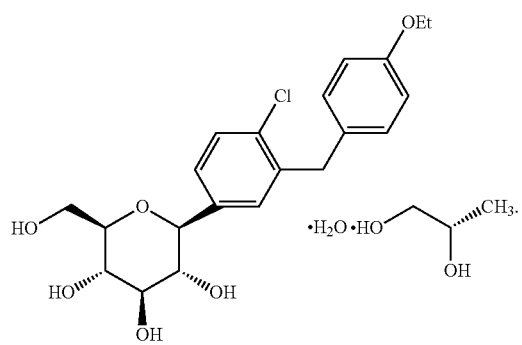

24. The formulation according to claim 1, wherein the formulation comprises:
a) dapagliflozin propylene glycol hydrate, wherein the dapagliflozin propylene glycol hydrate is present in an amount within the range of from about 0.1% to about 15% by weight of tablet or capsule fill;
b) microcrystalline cellulose, wherein the microcrystalline cellulose is present in an amount sufficient to make the total weight of the tablet or capsule fill 100%;
c) lactose, wherein the lactose is present in an amount within the range of from about 10% to about 30% by weight of tablet or capsule fill;
d) crospovidone, wherein the crospovidone is present in an amount within the range of from about 3% to about 10% by weight of tablet or capsule fill;
e) silicon dioxide, wherein the silicon dioxide is present in an amount within the range of from about 0.5% to about 4% by weight of tablet or capsule fill; and
f) magnesium stearate, wherein the magnesium stearate is present in an amount within the range of from about 0.5% to about 2% by weight of tablet or capsule fill.

25. The formulation according to claim 24, wherein the dapagliflozin propylene glycol hydrate is the (S)-propylene glycol hydrate having the formula

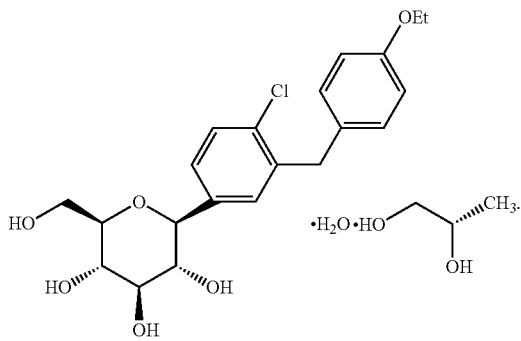

26. The formulation according to claim 1, wherein said formulation is in the form of a 1.0 mg dapagliflozin dose tablet comprising:
   a) dapagliflozin propylene glycol hydrate, wherein the dapagliflozin propylene glycol hydrate is present in an amount of 1.23 mg;
   b) microcrystalline cellulose, wherein the microcrystalline cellulose is present in an amount of about 50 mg to about 90 mg;
   c) lactose, wherein the lactose is present in an amount of about 10 mg to about 30 mg;
   d) crospovidone, wherein the crospovidone is present in an amount of about 2 mg to about 10 mg;
   e) silicon dioxide, wherein the silicon dioxide is present in an amount of about 0.5 mg to about 4.0 mg;
   f) magnesium stearate, wherein the magnesium stearate is present in an amount of about 0.5 mg to about 2.0 mg; and
   g) an antioxidant and/or chelating agent, wherein the antioxidant and/or chelating agent is present in an amount of about 0 mg to about 0.5 mg.

27. The formulation according to claim 26, wherein the dapagliflozin propylene glycol hydrate is the (S)-propylene glycol hydrate having the formula

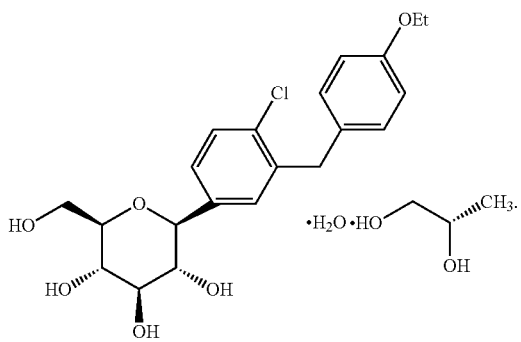

28. The formulation according to claim 1, wherein said formulation is in the form of a 2.5 mg dapagliflozin dose tablet comprising:
   a) dapagliflozin propylene glycol hydrate, wherein the dapagliflozin propylene glycol hydrate is present in an amount of 3.075 mg;
   b) microcrystalline cellulose, wherein the microcrystalline cellulose is present in an amount of about 60 mg to about 115 mg;
   c) lactose, wherein the lactose is present in an amount of about 12.5 mg to about 38 mg;
   d) crospovidone, wherein the crospovidone is present in an amount of about 2.5 mg to about 13 mg;
   e) silicon dioxide, wherein the silicon dioxide is present in an amount of about 0.6 mg to about 5.0 mg;
   f) magnesium stearate, wherein the magnesium stearate is present in an amount of about 0.6 mg to about 2.5 mg; and
   g) an antioxidant and/or chelating agent, wherein the antioxidant and/or chelating agent is present in an amount of about 0 mg to about 0.6 mg.

29. The formulation according to claim 28, wherein the dapagliflozin propylene glycol hydrate is the (S)-propylene glycol hydrate having the formula

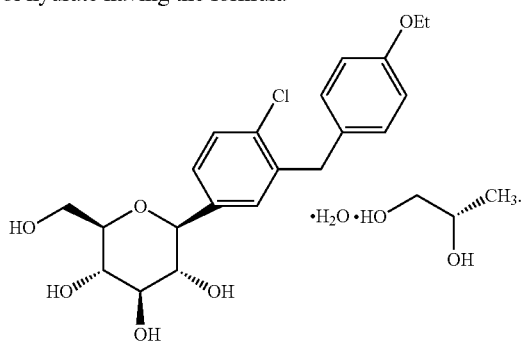

30. The formulation according to claim 1, wherein said formulation is in the form of a 5.0 mg dapagliflozin dose tablet comprising:
   a) dapagliflozin propylene glycol hydrate, wherein the dapagliflozin propylene glycol hydrate is present in an amount of 6.15 mg;
   b) microcrystalline cellulose, wherein the microcrystalline cellulose is present in an amount of about 60 mg to about 115 mg;
   c) lactose, wherein the lactose is present in an amount of about 12.5 mg to about 38 mg;
   d) crospovidone, wherein the crospovidone is present in an amount of about 2.5 mg to about 13 mg;
   e) silicon dioxide, wherein the silicon dioxide is present in an amount of about 0.6 mg to about 5.0 mg;
   f) magnesium stearate, wherein the magnesium stearate is present in an amount of about 0.6 mg to about 2.5 mg; and
   g) an antioxidant and/or chelating agent, wherein the antioxidant and/or chelating agent is present in an amount of about 0 mg to about 0.6 mg.

31. The formulation according to claim 30, wherein the dapagliflozin propylene glycol hydrate is the (S)-propylene glycol hydrate having the formula

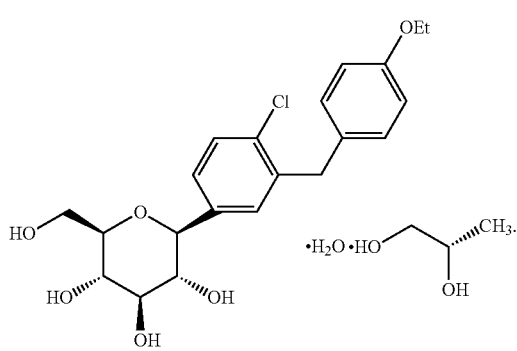

32. The formulation according to claim 1, wherein said formulation is in the form of a 10 mg dapagliflozin dose tablet comprising:
   a) dapagliflozin propylene glycol hydrate, wherein the dapagliflozin propylene glycol hydrate is present in an amount of 12.3 mg;
   b) microcrystalline cellulose, wherein the microcrystalline cellulose is present in an amount of about 120 mg to about 230 mg;
   c) lactose, wherein the lactose is present in an amount of about 25 mg to about 75 mg;
   d) crospovidone, wherein the crospovidone is present in an amount of about 5 mg to about 25 mg;
   e) silicon dioxide, wherein the silicon dioxide is present in an amount of about 1.0 mg to about 10 mg;
   f) magnesium stearate, wherein the magnesium stearate is present in an amount of about 1.0 mg to about 5 mg; and
   g) an antioxidant and/or chelating agent, wherein the antioxidant and/or chelating agent is present in an amount of about 0 mg to about 1.25 mg.

33. The formulation according to claim 32, wherein the dapagliflozin propylene glycol hydrate is the (S)-propylene glycol hydrate having the formula

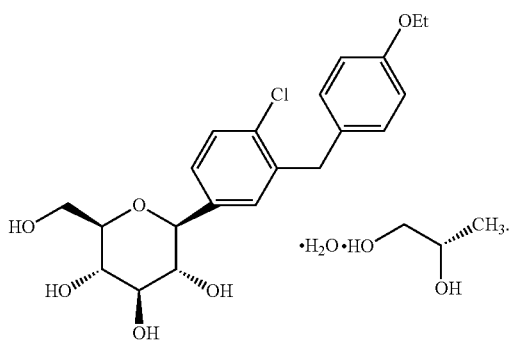

34. The formulation according to claim 1, comprising:
   a) dapagliflozin propylene glycol hydrate, wherein the dapagliflozin propylene glycol hydrate is present in an amount within the range of from about 0.1% to about 15% by weight of tablet or capsule fill;
   b) microcrystalline cellulose, wherein the microcrystalline cellulose is present in an amount sufficient to make the total weight of the tablet or capsule fill 100%;
   c) lactose, wherein the lactose is present in an amount within the range of from about 10% to about 30% by weight of tablet or capsule fill;
   d) crospovidone, wherein the crospovidone is present in an amount within the range of from about 3% to about 10% by weight of tablet or capsule fill;
   e) silicon dioxide, wherein the silicon dioxide is present in an amount within the range of from about 0.5% to about 4% by weight of tablet or capsule fill; and
   f) magnesium stearate, wherein the magnesium stearate is present in an amount within the range of from about 0.5% to about 2% by weight of tablet or capsule fill.

35. The formulation according to claim 1, in the form of a 1.0 mg tablet comprising:
   a) dapagliflozin propylene glycol hydrate, wherein the dapagliflozin propylene glycol hydrate is present in an amount of 1.23 mg;
   b) microcrystalline cellulose, wherein the microcrystalline cellulose is present in an amount of about 50 mg to about 90 mg;
   c) lactose, wherein the lactose is present in an amount of about 10 mg to about 30 mg;
   d) crospovidone, wherein the crospovidone is present in an amount of about 2 mg to about 10 mg;
   e) silicon dioxide, wherein the silicon dioxide is present in an amount of about 0.5 mg to about 4.0 mg;
   f) magnesium stearate, wherein the magnesium stearate is present in an amount of about 0.5 mg to about 2.0 mg; and
   g) an antioxidant and/or chelating agent, wherein the antioxidant and/or chelating agent is present in an amount of about 0 mg to about 0.5 mg.

36. The formulation according to claim 1, in the form of a 2.5 mg tablet comprising:
   a) dapagliflozin propylene glycol hydrate, wherein the dapagliflozin propylene glycol hydrate is present in an amount of 3.075 mg;
   b) microcrystalline cellulose, wherein the microcrystalline cellulose is present in an amount of about 60 mg to about 115 mg;
   c) lactose, wherein the lactose is present in an amount of about 12.5 mg to about 38 mg;
   d) crospovidone, wherein the crospovidone is present in an amount of about 2.5 mg to about 13 mg;
   e) silicon dioxide, wherein the silicon dioxide is present in an amount of about 0.6 mg to about 5.0 mg;
   f) magnesium stearate, wherein the magnesium stearate is present in an amount of about 0.6 mg to about 2.5 mg; and
   g) an antioxidant and/or chelating agent, wherein the antioxidant and/or chelating agent is present in an amount of about 0 mg to about 0.6 mg.

37. The formulation according to claim 1, in the form of a 5.0 mg tablet comprising:
   a) dapagliflozin propylene glycol hydrate, wherein the dapagliflozin propylene glycol hydrate is present in an amount of 6.15 mg;
   b) microcrystalline cellulose, wherein the microcrystalline cellulose is present in an amount of about 60 mg to about 115 mg;
   c) lactose, wherein the lactose is present in an amount of about 12.5 mg to about 38 mg;
   d) crospovidone, wherein the crospovidone is present in an amount of about 2.5 mg to about 13 mg;
   e) silicon dioxide, wherein the silicon dioxide is present in an amount of about 0.6 mg to about 5.0 mg;
   f) magnesium stearate, wherein the magnesium stearate is present in an amount of about 0.6 mg to about 2.5 mg; and
   g) an antioxidant and/or chelating agent, wherein the antioxidant and/or chelating agent is present in an amount of about 0 mg to about 0.6 mg.

38. The formulation according to claim 1, in the form of a 10 mg tablet comprising:
   a) dapagliflozin propylene glycol hydrate, wherein the dapagliflozin propylene glycol hydrate is present in an amount of 12.3 mg;
   b) microcrystalline cellulose, wherein the microcrystalline cellulose is present in an amount of about 120 mg to about 230 mg;
   c) lactose, wherein the lactose is present in an amount of about 25 mg to about 75 mg;
   d) crospovidone, wherein the crospovidone is present in an amount of about 5 mg to about 25 mg;
   e) silicon dioxide, wherein the silicon dioxide is present in an amount of about 1.0 mg to about 10 mg;

f) magnesium stearate, wherein the magnesium stearate is present in an amount of about 1.0 mg to about 5 mg; and
g) an antioxidant and/or chelating agent, wherein the antioxidant and/or chelating agent is present in an amount of about 0 mg to about 1.25 mg.

* * * * *